US011672959B2

(12) United States Patent
Stankus et al.

(10) Patent No.: US 11,672,959 B2
(45) Date of Patent: Jun. 13, 2023

(54) EXPANDABLE MEMBER SYSTEMS AND METHODS FOR DRUG DELIVERY

(71) Applicant: Intersect ENT, Inc., Menlo Park, CA (US)

(72) Inventors: John Joseph Stankus, San Jose, CA (US); James Su, Newark, CA (US)

(73) Assignee: Intersect ENT, Inc., Menlo Park, CA (US)

( * ) Notice: Subject to any disclaimer, the term of this patent is extended or adjusted under 35 U.S.C. 154(b) by 0 days.

(21) Appl. No.: 16/745,110

(22) Filed: Jan. 16, 2020

(65) Prior Publication Data

US 2020/0230373 A1 Jul. 23, 2020

Related U.S. Application Data

(60) Provisional application No. 62/794,363, filed on Jan. 18, 2019.

(51) Int. Cl.
*A61M 25/10* (2013.01)
*A61L 29/06* (2006.01)
(Continued)

(52) U.S. Cl.
CPC ............ *A61M 25/10* (2013.01); *A61K 31/58* (2013.01); *A61L 29/06* (2013.01); *A61L 29/16* (2013.01);
(Continued)

(58) Field of Classification Search
CPC ................. A61K 2300/00; A61P 29/00; A61L 2300/606; A61M 2025/105
See application file for complete search history.

(56) References Cited

U.S. PATENT DOCUMENTS 5,209,732 A 5/1993 Lampropoulos et al.
5,562,619 A 10/1996 Mirarchi et al.
(Continued)

FOREIGN PATENT DOCUMENTS

CN 102458497 A 5/2012
CN 102458555 A 5/2012
(Continued)

OTHER PUBLICATIONS

Ketan, et al, "Drug Solubility: Importance and Enhancement Techniques" 2012, ISRN Pharmaceutics, 2012: 195727. (Year: 2012).*
(Continued)

*Primary Examiner* — Laura A Bouchelle
(74) *Attorney, Agent, or Firm* — Carter, DeLuca & Farrell LLP

(57) ABSTRACT

Described here are systems and methods for delivering an active agent to target tissues of the ear, nose, or throat using an expandable member having drug crystals layered thereon, and methods for manufacturing such systems. The expandable member can be delivered to the target tissues in a low-profile configuration and expanded to contact and/or dilate surrounding tissue. Expansion of the expandable member transfers the drug crystals to the target tissues, which then act as an in situ depot that enables maintenance of a therapeutic level of an active agent for a desired time period after removal of the expandable member. Multiple expansions of a single expandable member can be employed during treatment. For example, the systems and methods can be useful when it is desired to treat multiple paranasal sinuses with a single expandable member.

12 Claims, 8 Drawing Sheets

(51) Int. Cl.
*A61L 29/16* (2006.01)
*A61K 31/58* (2006.01)

(52) U.S. Cl.
CPC .... *A61M 25/1029* (2013.01); *A61L 2300/216* (2013.01); *A61M 2025/105* (2013.01); *A61M 2025/1031* (2013.01); *A61M 2210/065* (2013.01); *A61M 2210/0618* (2013.01); *A61M 2210/0656* (2013.01); *A61M 2210/0662* (2013.01); *A61M 2210/0668* (2013.01); *A61M 2210/0675* (2013.01); *A61M 2210/0681* (2013.01); *A61M 2210/105* (2013.01); *A61M 2210/1028* (2013.01); *A61M 2210/1032* (2013.01)

(56) References Cited

U.S. PATENT DOCUMENTS

| | | | |
|---|---|---|---|
| 5,702,754 | A | 12/1997 | Zhong |
| 6,329,386 | B1 | 12/2001 | Mollison |
| 6,533,772 | B1 | 3/2003 | Sherts et al. |
| 7,105,013 | B2 | 9/2006 | Durcan |
| 7,559,925 | B2 | 7/2009 | Goldfarb et al. |
| 7,717,933 | B2 | 5/2010 | Becker |
| 7,740,642 | B2 | 6/2010 | Becker |
| 7,753,929 | B2 | 7/2010 | Becker |
| 7,771,409 | B2 | 8/2010 | Chang et al. |
| 7,803,150 | B2 | 9/2010 | Chang et al. |
| 8,100,933 | B2 | 1/2012 | Becker |
| 8,142,422 | B2 | 3/2012 | Makower et al. |
| 8,414,473 | B2 | 4/2013 | Jenkins et al. |
| 8,777,926 | B2 | 7/2014 | Chang et al. |
| 8,801,662 | B2 | 8/2014 | Manish et al. |
| 8,858,586 | B2 | 10/2014 | Chang et al. |
| 8,905,922 | B2 | 12/2014 | Makower et al. |
| 9,138,569 | B2 | 9/2015 | Edgren et al. |
| 9,381,328 | B2 | 7/2016 | Xie et al. |
| 9,471,850 | B2 | 10/2016 | Krueger |
| 9,554,817 | B2 | 1/2017 | Goldfarb et al. |
| 9,603,506 | B2 | 3/2017 | Goldfarb et al. |
| 10,022,525 | B2 | 7/2018 | Hanson |
| 10,105,315 | B2 * | 10/2018 | Meltzer .................. A61P 37/08 |
| 10,166,369 | B2 | 1/2019 | Jenkins et al. |
| 10,238,846 | B2 | 3/2019 | Ressemann |
| 10,441,757 | B2 | 10/2019 | Kaufman et al. |
| 10,524,814 | B2 | 1/2020 | Chang et al. |
| 10,603,473 | B2 | 3/2020 | Kaufman et al. |
| 10,688,289 | B2 | 6/2020 | Finson et al. |
| 10,814,108 | B2 | 10/2020 | Kaufman et al. |
| 2002/0082584 | A1 | 6/2002 | Rosenman et al. |
| 2006/0004286 | A1 | 1/2006 | Chang et al. |
| 2007/0250105 | A1 | 10/2007 | Ressemann et al. |
| 2008/0065011 | A1 | 3/2008 | Marchand et al. |
| 2009/0082368 | A1 * | 3/2009 | Vohra .................. C07D 403/14 514/257 |
| 2009/0163890 | A1 | 6/2009 | Clifford et al. |
| 2009/0226502 | A1 | 9/2009 | Chen |
| 2010/0113939 | A1 | 5/2010 | Mashimo et al. |
| 2010/0198190 | A1 | 8/2010 | Michal et al. |
| 2010/0198191 | A1 * | 8/2010 | Clifford .................. A61B 8/12 604/514 |
| 2010/0211007 | A1 | 8/2010 | Lesch, Jr. et al. |
| 2010/0272773 | A1 | 10/2010 | Kangas et al. |
| 2010/0274188 | A1 | 10/2010 | Chang et al. |
| 2011/0144577 | A1 | 6/2011 | Stankus et al. |
| 2012/0143054 | A1 | 6/2012 | Eaton et al. |
| 2012/0143132 | A1 | 6/2012 | Orlowski |
| 2012/0150142 | A1 | 6/2012 | Weber et al. |
| 2013/0053947 | A1 | 2/2013 | Kangas et al. |
| 2013/0066358 | A1 | 3/2013 | Nalluri et al. |
| 2013/0085472 | A1 | 4/2013 | Shaari |
| 2013/0142834 | A1 | 6/2013 | Esfand et al. |
| 2014/0018732 | A1 | 1/2014 | Bagaosian |
| 2014/0046255 | A1 | 2/2014 | Hakimimehr et al. |
| 2014/0073911 | A1 | 3/2014 | Munrow et al. |
| 2014/0074140 | A1 | 3/2014 | Johnson et al. |
| 2014/0100445 | A1 | 4/2014 | Stenzel et al. |
| 2014/0200443 | A1 | 7/2014 | Chang et al. |
| 2015/0065810 | A1 | 3/2015 | Edgren et al. |
| 2015/0112134 | A1 | 4/2015 | Suehara et al. |
| 2015/0142046 | A1 | 5/2015 | Andersen et al. |
| 2015/0165176 | A1 | 6/2015 | Makower |
| 2015/0182732 | A1 * | 7/2015 | Zeng .................. A61M 25/1029 604/103.02 |
| 2015/0273117 | A1 | 10/2015 | Wang |
| 2016/0045718 | A1 | 2/2016 | Pruitt et al. |
| 2016/0121088 | A1 | 5/2016 | Fox et al. |
| 2016/0144158 | A1 | 5/2016 | Abbate |
| 2016/0213890 | A1 * | 7/2016 | Kaufman .............. A61L 29/085 |
| 2016/0287342 | A1 | 10/2016 | Jacobsen et al. |
| 2017/0028112 | A1 | 2/2017 | Drontle et al. |
| 2017/0165064 | A1 | 6/2017 | Nyuli et al. |
| 2018/0036009 | A1 | 2/2018 | Zoabi et al. |
| 2018/0104461 | A1 | 4/2018 | Matlock |
| 2018/0344202 | A1 | 12/2018 | Bar-Tal |
| 2019/0160266 | A1 | 5/2019 | Ngo-Chu et al. |
| 2019/0374751 | A1 | 12/2019 | Finson et al. |
| 2020/0179659 | A1 | 6/2020 | Kaufman et al. |
| 2020/0276422 | A1 | 9/2020 | Finson et al. |
| 2020/0391013 | A1 | 12/2020 | Kaufman et al. |
| 2022/0047854 | A1 | 2/2022 | Mucha et al. |

FOREIGN PATENT DOCUMENTS

| | | |
|---|---|---|
| CN | 102847200 B | 1/2013 |
| DE | 102011119073 A1 | 5/2013 |
| EP | 0691663 A1 | 1/1996 |
| JP | 8-317970 A | 12/1996 |
| JP | 2008-099917 A | 5/2008 |
| JP | 2011-528275 A | 11/2011 |
| JP | 2013-515591 A | 5/2013 |
| JP | 2014-200269 A | 10/2014 |
| WO | WO-2006/107957 A2 | 10/2006 |
| WO | WO-2006/107957 A3 | 10/2006 |
| WO | WO-2010/009335 A1 | 1/2010 |
| WO | WO-2010/121840 A2 | 10/2010 |
| WO | WO-2010/121840 A3 | 10/2010 |
| WO | WO-2010/126912 A1 | 11/2010 |
| WO | WO-2010/132648 A1 | 11/2010 |
| WO | WO 2010/132648 A1 | 11/2010 |
| WO | WO 2010/140163 A2 | 12/2010 |
| WO | WO2010140163 A2 | 12/2010 |
| WO | WO-2011/082139 A1 | 7/2011 |
| WO | WO-2013/130464 A1 | 9/2013 |
| WO | WO-2014/066085 A1 | 5/2014 |
| WO | WO-2014/075513 A1 | 5/2014 |
| WO | WO-2016/118923 A1 | 7/2016 |
| WO | WO-2020/221882 A1 | 11/2020 |

OTHER PUBLICATIONS

Sangolkar et al.; Particle size determination of nasal drug delivery system: a review; Int. J. Pharm. Sci. Rev. Res., 17(1), 2012, 66-73) (Year: 2012).*
Extended European Search Report dated Dec. 5, 2018, for EP Application No. 16 740 876.4, filed on Jan. 22, 2016, 9 pages.
Final Office Action dated Apr. 11, 2019, for U.S. Appl. No. 15/004,807, filed Jan. 22, 2016, 12 pages.
Final Office Action dated Jan. 14, 2020, for U.S. Appl. No. 16/436,363, filed Jun. 10, 2019, 6 pages.
International Search Report dated Mar. 31, 2016, for PCT Application No. PCT/US2016/014622, filed Jan. 22, 2016, 2 pages.
International Search Report dated Aug. 28, 2019, for PCT Application No. PCT/US2019/036506, filed Jun. 11, 2019, 3 pages.
International Search Report dated Apr. 7, 2020, for PCT Application No. PCT/US2020/014090, filed Jan. 17, 2020, 2 pages.
Non-Final Office Action dated Dec. 31, 2018, for U.S. Appl. No. 15/004,807, filed Jan. 22, 2016, 10 pages.
Non-Final Office Action dated Aug. 30, 2019, for U.S. Appl. No. 16/436,363, filed Jun. 10, 2019, 9 pages.
Non-Final Office Action dated Mar. 20, 2020, for U.S. Appl. No. 16/790,464, filed Feb. 13, 2020, 6 pages.

(56) References Cited

OTHER PUBLICATIONS

Notice of Allowance dated Jul. 17, 2019, for U.S. Appl. No. 15/004,807, filed Jan. 22, 2016, 7 pages.
Notice of Allowance dated Aug. 13, 2019, for U.S. Appl. No. 15/004,807, filed Jan. 22, 2016, 6 pages.
Notice of Allowance dated Nov. 22, 2019, for U.S. Appl. No. 16/523,836, filed Jul. 26, 2019, 7 pages.
Notice of Allowance dated Feb. 27, 2020, for U.S. Appl. No. 16/436,363, filed Jun. 10, 2019, 5 pages.
St. Croix, B. et al. (2000). "Genes expressed in human tumor endothelium," *Science* 289:1197-1202.
Written Opinion of the International Searching Authority dated Mar. 31, 2016, for PCT Application No. PCT/US2016/014622, filed Jan. 22, 2016, 7 pages.
Written Opinion of the International Searching Authority dated Aug. 28, 2019, for PCT Application No. PCT/US2019/036506, filed Jun. 11, 2019, 12 pages.
Written Opinion of the International Searching Authority dated Apr. 7, 2020, for PCT Application No. PCT/US2020/014090, filed Jan. 17, 2020, 8 pages.
Notice of Allowance dated Jun. 4, 2020, for U.S. Appl. No. 16/790,464, filed Feb. 13, 2020, 7 pages.
Corrected Notice of Allowability dated Sep. 29, 2020, for U.S. Appl. No. 16/790,464, filed Feb. 13, 2020, 4 pages.
Croix et al., Genes expressed in human tumor endothelium, Science, Aug. 18, 2000, pp. 1197-1202, vol. 289.
European Patent Office, International Search Report and Written Opinion for PCT/EP2020/062083, dated Aug. 7, 2020, 14 pages.
Savjai et al, Drug Solubility: Importance and Enhancement Techniques, International Scholarly Research Notices, 2012, 10 pages, vol. 2012, Article ID 195727.
The United States Patent and Trademark Office, Non-Final Office Action for U.S. Appl. No. 15/004,807, dated Dec. 31, 2018, 9 pages.
The United States Patent and Trademark Office, Final Office Action for U.S. Appl. No. 15/004,807, dated Apr. 11, 2019, 11 pages.
The United States Patent and Trademark Office, Notice of Allowance for U.S. Appl. No. 15/004,807, dated Jul. 17, 2019, 7 pages.
The United States Patent and Trademark Office, Non-Final Office Action for U.S. Appl. No. 16/436,363, dated Aug. 30, 2019, 8 pages.
The United States Patent and Trademark Office, Notice of Allowance for U.S. Appl. No. 16/436,363, dated Feb. 27, 2020, 5 pages.
The United States Patent and Trademark Office, International Search Report and Written Opinion for PCT Application No. PCT/US2020/014090, dated Apil 7, 2020, 10 pages.
The United States Patent and Trademark Office, Non-Final Office Action for U.S. Appl. No. 16/790,464, dated Mar. 20, 2020, 5 pages.
The United States Patent and Trademark Office, Notice of Allowance for U.S. Appl. No. 16/790,464, dated Sep. 29, 2020, 4 pages.
The International Bureau of WIPO, International Preliminary Report on Patentability for PCT Application No. PCT/US2016/014622, dated Jul. 25, 2017, 8 pages.
Extended European Search Report issued in corresponding European Application No. 20741615.7 dated Aug. 23, 2022, 7 pages.
Russian Office Action issued in corresponding Russian Application No. 202191843/28 dated Oct. 19, 2022, 11 pages.

\* cited by examiner

Square Balloon

Tapered Balloon

Conical/Square Balloon

Stepped Balloon

Conical/Spherical Balloon

Conical/Offset Balloon

EXPANDABLE MEMBER SYSTEMS AND METHODS FOR DRUG DELIVERY

RELATED APPLICATIONS

This application claims benefit of priority to U.S. provisional application 62/794,363, filed on Jan. 18, 2019, which is hereby incorporated by reference in its entirety. U.S. Pat. No. 10,441,757, filed on Jan. 22, 2016 and U.S. patent application Ser. No. 16/436,363, filed on Jun. 10, 2019, are both also hereby incorporated by reference in their entirety.

FIELD

This application generally relates to systems and methods for delivering one or more active agents to target tissues of the nose, ear, and throat. The systems and methods employ drug crystals layered on the outer surface of an expandable member in varying amounts and sizes. Upon expansion of the expandable member, the drug crystals are transferred to a target tissue and form a depot for sustained release of the active agent over a period of time effective to treat a nasal, otic, or throat condition.

BACKGROUND

Rhinosinusitis is a common paranasal sinus condition that is generally understood as encompassing sinusitis and/or rhinitis. Typically, rhinosinusitis is characterized by symptoms such as nasal discharge, nasal obstruction, facial congestion, facial pain/pressure, loss of smell, fever, and headache. Allergic rhinitis, another common paranasal sinus condition, is associated with a group of symptoms affecting the nose that occurs when an individual with the condition breaths in an allergen, such as dust, mold, or animal dander. Allergens cause the release of histamine, which usually causes sneezing, itchy and watery eyes, runny nose, swelling and inflammation of the nasal passages, an increase in mucus production, and for some individuals, hives or other rashes.

Current treatments for these and other nasal conditions, as well as certain otic and throat conditions, are primarily pharmaceutical. Drugs in pill form are widely available and easy to take, but can have several drawbacks. An orally administered drug can require considerable time to work through the body to become effective, and can have negative side effects that can impact the daily life of the patient. Additionally, the drug can need to be taken frequently for continued symptom relief. Nasal, otic, and throat topical drug delivery represents an attractive alternative approach for the treatment of local nasal, otic, and throat diseases. However, current technologies for local drug delivery of drugs in either liquid or powder form, and by spray or direct (e.g., topical) application, can be limited by poor patient compliance when repeated doses are required, or poor efficacy due to challenges in delivering a drug to more distal tissues of the sinus, ear, and throat.

Another challenge with topical drug delivery is presented when the nasal, otic, or throat condition involves treatment of mucosal tissue. Most mucosal epithelial tissues are covered with a glycoprotein rich mucus layer. This mucus layer is a dynamic layer that generally has a turnover time of approximately 15-20 minutes. A locally delivered drug must pass through this mucus layer and be taken up by the mucosal epithelium before it is moved away from the target tissue site. The crystal form of drugs can be beneficial when attempting to deliver certain drugs, e.g., poorly soluble drugs, into mucosal tissue given that it can enhance saturation solubility, dissolution velocity, and adhesiveness to mucosal tissue.

Accordingly, when mucosal tissues are affected in the nose, ear, or throat, e.g., the paranasal sinuses, it can be beneficial to have topical treatments where the crystalline form of drugs is employed. Additionally, it can be useful to have treatments that can both deliver drugs and dilate target tissues such as the paranasal sinuses. It can also be useful to have treatments capable of delivering drugs to multiple sites with a single device.

SUMMARY

Described herein are systems and methods for locally delivering a therapeutically effective amount of an active agent to target tissues of the nose, ear, and throat. The systems and methods generally employ an expandable member that delivers the active agent upon expansion and contact with the target tissue. To facilitate absorption or uptake of the active agent into the target tissue before it is cleared by mucociliary flow, the active agent can be provided as drug crystals in an amount and size on the expandable member that facilitates target tissue uptake. In turn, the drug crystals taken up by the target tissue function as a sustained release depot or reservoir that enables maintenance of a therapeutic level of drug for a desired time frame (e.g., days, weeks, or months). The time period will typically be of a duration effective to treat an ear, nose, or throat condition. It is understood that the terms "drug" and "active agent" are used interchangeably throughout. The expandable member can be an inflatable balloon.

In some variations, the systems for locally delivering a therapeutically effective amount of an active agent to a target tissue can include an expandable member sized and shaped for placement in an ear, nose, or throat of a patient, the expandable member including a drug layer at least partially covering an outer surface thereof, where the drug layer has at least about 60% of the active agent as drug crystals, and where the drug crystals have an average length greater than about 80 µm. In variations where the drug layer has at least about 60% of the active agent as drug crystals, the drug crystals can also have an average length greater than about 90 µm, greater than about 100 µm, greater than about 110 µm, greater than about 120 µm, or greater than about 130 µm. When the drug crystals have an average length of about 130 µm, it can be beneficial for the drug layer to have at least about 65% of the active agent as drug crystals. It can be useful to include drug crystals having average lengths greater than about 80 µm in the drug layer when drug release is desired over longer time periods, for example, at least about 30 days.

In other variations, the systems for locally delivering a therapeutically effective amount of an active agent to a target tissue includes an expandable member sized and shaped for placement in an ear, nose, or throat of a patient, the expandable member including a drug layer at least partially covering an outer surface thereof, where the drug layer has less than about 60% of the active agent as drug crystals, and where the drug crystals have an average length of less than about 80 µm. In variations where the drug crystals have an average length less than about 80 µm, the drug layer can have less than about 55%, less than about 50%, less than about 45%, less than about 40%, less than about 35%, less than about 30%, less than about 25%, or less than about 20% of the active agent as drug crystals. It can be useful to include drug crystals having average lengths less than about 80 µm in the drug layer when drug release is desired over shorter time periods, for example, less than about 14 days.

The methods described herein can include locally delivering a therapeutically effective amount of an active agent to a target tissue by: 1) advancing an expandable member to a location within the ear, nose, or throat of the patient, the expandable member including a low-profile configuration and an expanded configuration, and a drug layer at least partially covering an outer surface of the expandable member, the drug layer including an active agent in the form of drug crystals; and 2) delivering the drug crystals to the target tissue by expanding the expandable member from the low-profile configuration to the expanded configuration so that the drug crystals contact the target tissue and form a depot in the target tissue that provides sustained release of the active agent for a period of time effective to treat a nasal, otic, or throat condition. Expansion can include either a single expansion and collapse of the expandable member or multiple expansion-collapse cycles (e.g., inflation-deflation cycles) of the same expandable member. When the drug layer has less than about 60% of the active agent as drug crystals, the drug crystals can have an average length of less than about 80 µm. When the drug layer has at least about 60% of the active agent as drug crystals, the drug crystals can have an average length greater than about 80 µm. Other combinations of drug crystal amount in the drug layer and average drug crystal length can be used.

In addition to containing drug crystals, the drug layer can also include the amorphous form of the active agent. Any active agent used to treat an ear, nose, or throat condition can be included in the drug layer, e.g., a corticosteroid can be employed. Mometasone furoate can be a useful corticosteroid to treat rhinosinusitis, polypoid edema, and general inflammation of the tissue at a target site. The drug layer can further include excipients such as a poly(vinyl pyrrolidone), a polysorbate, a poly(ethylene glycol), propylene glycol, glycerol caproate, or combinations or mixtures thereof. In one variation, the drug layer can include crystals of mometasone furoate, a polysorbate, and poly(ethylene glycol). In another variation, the drug layer can include less than about 60% of the mometasone furoate as drug crystals, a polysorbate, and poly(ethylene glycol). In another variation, the drug layer can include at least about 60% of the mometasone furoate as drug crystals, a polysorbate, and poly(ethylene glycol).

Some variations of the system and method include transferring substantially all the drug crystals from the expandable member to the target tissue with a single expansion. In other variations, the system and method includes using a single expandable member to treat multiple target tissue sites. For example, a single expandable member could be used to treat multiple sinuses (e.g., six different sinus ostia) in a patient. Here the drug layer can be formulated so that only a portion of the layer (and a portion of the drug crystals) is transferred with each expansion. The drug layer can also be configured, e.g., as multiple layers (sub-layers), to transfer one or more drugs over multiple expansions. Various surface treatments, e.g., plasma treatment or a hydrophilic primer layer, can also be applied to the expandable member to manipulate drug layer transfer rates. The expandable member can also be employed in systems and methods where it can beneficial to both dilate and deliver drugs to the target tissue.

The expandable members can be used to treat inflammation of mucosal tissue, e.g., mucociliary tissue, which is present in the nasal passages and sinuses, among other structures of the respiratory system. In some variations, the condition to be treated can be a nasal condition selected from the group consisting of post-surgical inflammation, rhinosinusitis, chronic sinusitis with or without nasal polyps, polypoid edema, and rhinitis, including allergic rhinitis. In such variations, the target tissue site can be a paranasal sinus, a sinus ostium, an inferior turbinate, a middle turbinate, a superior turbinate, a nasal cavity, the osteomeatal complex, the nasopharynx, adenoid tissue, or a combination thereof.

In other variations, the condition to be treated can be an otic condition selected from the group consisting of post-surgical inflammation, otitis media, Meniere's disease, Eustachian tube dysfunction, and tinnitus. In such variations, the target tissue site can be the Eustachian tube, external ear canal, or inner ear. Treatment of the Eustachian tube can also be beneficial in treating hearing loss, otalgia, and vertigo.

In other variations, the condition to be treated can be a throat condition selected from the group consisting of post-surgical pain, esophageal cancer, airway stenosis, e.g., tracheal stenosis or subglottic stenosis, chronic laryngitis, tonsillitis, and epiglottitis.

During manufacturing, the expandable member, e.g., a balloon, can be coated with a drug layer formulation by methods such as spray coating, pipette or syringe coating, or dip coating. For improved drug layer adhesion, the expandable member can be cleaned with a solvent and dried prior to coating. In addition, plasma treatment with an inert gas (such as argon) or oxygen after cleaning can increase the cleaning and wettability of the expandable member surface leading to increased drug layer adhesion and improved release of the layer upon contact with mucus at the mucosal tissue site. In some variations, the manufacturing method can include cleaning the balloon surface and/or treating the balloon with plasma, inflating the balloon, spray coating the balloon with a drug layer formulation, drying the balloon coating at room temperature or elevated temperature, and re-folding the balloon. In other variations, the manufacturing method can include cleaning the balloon surface and/or treating the balloon with plasma, inflating the balloon, spray coating the balloon with a drug layer formulation, exposing the coated balloon to a solvent vapor (solvent vapor annealing), and re-folding the balloon.

Varying the environmental conditions during the drug layer process can affect the rate of drug release from the expandable member. Certain conditions can favor crystal or amorphous forms of the drug. In some variations, the drug layer is exposed to a solvent vapor after application to modify the drug form in the layer, e.g., to produce more crystalline (non-amorphous) drug. Accordingly, by manipulating various conditions, drug release can be tailored to the particular indication and/or anatomy being treated.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

FIG. 5A shows the expandable member in its low-profile, folded/pleated configuration and FIG. 5B shows the expandable member in its expanded configuration.

DETAILED DESCRIPTION

Figure 1A:
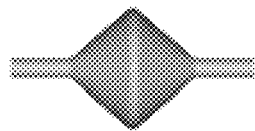
FIGS. 1A-1N depict exemplary shapes for the expandable member.

Described here are systems and methods for delivering an active agent to target tissues of the ear, nose, or throat using an expandable member having drug crystals layered thereon. The expandable member can be delivered to the target tissue in a low-profile configuration and then expanded to contact and/or dilate surrounding tissue. Expansion of the expandable member transfers the drug crystals to the target tissue, which then acts as an in situ depot, enabling maintenance of a therapeutic concentration of an active agent for a desired time period after removal of the expandable member. The systems and methods can be useful when drug delivery to mucosal tissues, e.g., the paranasal sinuses, is desired. Methods for manufacturing are also described herein.

The drug crystals are generally contained in a drug layer disposed on an outer surface of the expandable member. In variations where the drug crystals are larger, e.g., having an average length greater than about eighty micrometers (>80 µm), it can be beneficial for the expandable members to include a drug layer having at least about 60% of the active agent as drug crystals in order to achieve a therapeutically effective amount of the active agent in the target tissue. In variations where the drug crystals are smaller, e.g., having an average length less than about eighty micrometers (<80 µm), therapeutic levels of an active agent in a target tissue can be achieved using expandable members including a drug layer having less than about 60% of the active agent as drug crystals. It should be appreciated that in some cases, relatively smaller crystals in a drug layer covering about 50% (or less) of an expandable member can continue to grow during the manufacturing process, such that the crystal size and percentage of crystalline coverage increases for the finished device. Therapeutically effective amounts will vary based upon the particular active agent being delivered. In the case of mometasone furoate, a therapeutically effective amount is generally a mometasone furoate concentration in tissue of at least 0.1 µg/gm.

The expandable member can be expanded once or multiple times to deliver drug to the same target tissue or different target tissues. The systems can further include a delivery device to advance the expandable member to the target tissue. Generally, the treatment method can provide therapeutic levels of drug for a desired time period after expansion and removal of an expandable member.

The expandable member can have several applications. It can be adapted in size, configuration, and material for different uses, such as in the ear, nose, or throat. The expandable member can be useful in treating conditions involving mucosal inflammation. In some variations, the systems and methods can be used for treating one or more sinus or nasal conditions including, but not limited to rhinitis, allergic rhinitis, acute sinusitis, and chronic sinusitis with or without polyps, and polypoid edema, and all of which can have a mucosal inflammatory component. In other variations, the devices and methods can be implemented during a dilation procedure. For example, one or more drugs (e.g., a corticosteroid) can be delivered to reduce inflammation post ballooning, post dilation, or other surgery of the sinuses and/or sinus ostia. In other variations, one or more drugs can be delivered to the sinus and/or sinus ostia for relief of allergy symptoms. In another example, an expandable member, such as an inflatable balloon, can be used to deliver drugs to the inferior turbinate for the treatment of allergic rhinitis. In yet another example, the expandable member can be used for delivery of an anti-inflammatory (e.g., a corticosteroid) for reduction of inflammation post functional ethmoid surgery, including when mechanical support and a permanent implant may not be necessary.

In other variations, the systems and methods can be used for treating one or more conditions of the ear. For example, an expandable member can deliver drugs to the Eustachian tube post ballooning to treat Eustachian tube dysfunction. As another example, the expandable member can be used for drug delivery to the external ear canal for acute otitis media, chronic otitis media or swimmer's ear. The expandable member can also be used for drug delivery to the middle and/or inner ear for treatment of otitis media, Meniere's disease, tinnitus, or other applicable conditions.

In other variations, the expandable member can also have applications in the throat, where drug delivery can be for post-surgical pain, such as tonsillectomy pain, or for esophageal cancer, airway stenosis (e.g., tracheal stenosis or subglottic stenosis), chronic laryngitis, epiglottitis, other inflammatory diseases, and/or other conditions of the throat.

Devices

Expandable Members

The expandable members considered herein are generally coated with a therapeutic agent (drug) that may be physically transferred to the tissue site of interest upon expansion. The expandable members described herein are generally movable between a low-profile configuration and an expanded configuration. After therapeutic agent transfer, the expandable member may be collapsed and removed. The drug coating may be formulated to be transferred with a single expansion, or when multiple expansions with a single expandable member are performed, partially transferred with each expansion. The expandable members can have any suitable shape, in particular configured for a target anatomy or body lumen. When treating the Eustachian tube, it can be useful to have an expandable member shape that is cylindrical, conical, or tapered. In other variations, the expandable device may be combined with an implantable device, such as a stent or scaffold.

In some variations, the expandable members and/or components of an implantable device can be entirely bioabsorbable, entirely non-bioabsorbable, or partially bioabsorbable and non-bioabsorbable. When made to be bioabsorbable, the device can be formed from a bioabsorbable material selected from the group consisting of PLGA (poly(lactic-co-glycolic) acid), PLLA (poly(L-lactic acid)), PLA-PCL (poly(lactic acid)-polycaprolactone), PGA (poly(glycolic acid)), PDLLA (poly(D,L-lactic acid)), or combinations thereof. When made to be partially bioabsorbable, a coating on the device can be bioabsorbable and may or may not include a release rate modifier and/or a plasticizer such as PEG (polyethylene glycol).

The expandable members can include a flexible membrane configured to provide even and consistent contact with, and substantial coverage of, the surrounding tissue upon expansion. In some variations, the flexible membrane can be coupled to a tubular sheath that can be expanded using a mechanical system coupled to the internal surface of the tubular sheath. In other variations, the flexible membrane can have an inflatable structure that can be expanded using a fluid. For example, the inflatable structure can be a balloon, wherein the balloon can be expanded to an expanded configuration by delivery of a liquid (e.g., saline) or gas (e.g., air) to the interior of the balloon. In some variations, the expandable members can include a hub connecting the membrane to a shaft.

Figure 5A:
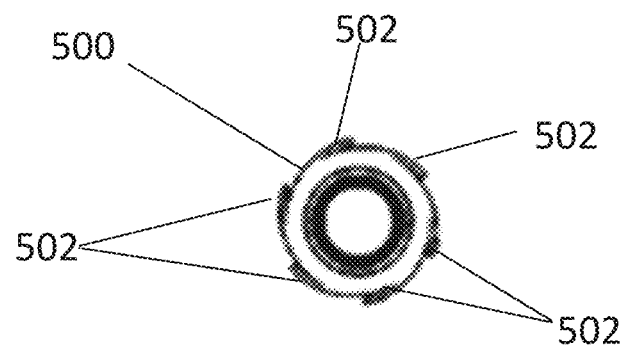
FIGS. 5A and 5B depict cross-sectional views of an exemplary expandable member having folds that protect against loss of drug crystals from the drug layer during deployment of the expandable member to a target tissue.
Figure 5B:
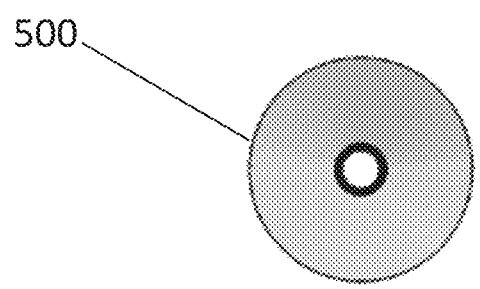

The low-profile configuration can be the expandable member in its collapsed state (or non-inflated state), or the expandable member pleated, folded, or wrapped upon itself. The number of pleats or folds can vary depending on, for example, the shape of the expandable member, the target tissue to be treated, and/or the intended number of expansions. Some variations of the expandable member include lateral, accordion-like pleats or folds. In other variations, the pleats or folds are arranged longitudinally (i.e., along the length of) the expandable member. In yet further variations, as shown in FIG. 5A, the expandable member is a cylindrical balloon (500) having six pleats or folds (502) when in the collapsed state. The pleats or folds can help with protecting against loss of the drug layer and drug crystals contained therein until the balloon reaches the target tissue and is expanded to the expanded state, as shown in FIG. 5B. The drug layer and drug crystals can uniformly coat the entire expandable member, partially coat the expandable member, or be provided only within the pleats or folds of the expandable member. In other instances, the low-profile configuration can be the expandable member in a partially collapsed (or partially inflated) state. A sheath or other covering can be used to cover the expandable member and also used to prevent loss of the drug layer and drug crystals during advancement of the expandable member to one or more target tissues. In one variation, a sheath or cover can constrain the expandable member in its low-profile configuration. In this variation, the expandable member can be self-expanding. In some variations, expansion to the expanded configuration is accomplished via inflation with a fluid or a gas.

The expandable member can be non-compliant, semi-compliant, or compliant. While the following description relating to compliance is primarily directed to a balloon, it can apply to expandable members of other forms and configurations. Balloon compliance is a term generally used to describe the degree to which the diameter of a balloon changes as a function of inflation pressure. The inflation pressure of the balloons can range from about 2 atm to about 25 atm, depending on the balloon type, as further described below. When used to deliver drug crystals and/or dilate sinus ostia, inflation pressures can range from about 2 atm to about 25 atm, from about 2 atm to about 12 atm, from about 6 atm to about 12 atm, or from about 6 atm to about 8 atm. The inflation pressure used to expand the balloon from the collapsed to the expanded state and contact tissue to deliver drug crystals can be lower than the inflation pressures used to dilate sinus ostia. Accordingly, different inflation pressures can be used when the procedure includes multiple expansions of the balloon.

Figure 1D:
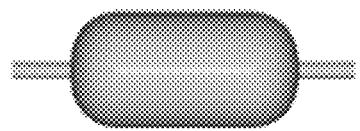
Figure 1B:
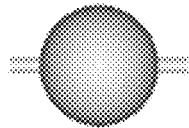

In some variations, the expandable member can be a compliant balloon. Compliant balloons can be made from materials having low (e.g., Shore A) durometer such as polyurethane, polyvinyl chloride (PVC), polyolefins, and other elastomers, and can be capable of increasing their diameter by about 100% to about 600% as inflation volume of the balloon increases. Compliant balloons typically have an inflation pressure less than about 16 atm. The compliant balloons can have any suitable shape, e.g., as shown in FIGS. 1A-1N. In some variations, compliant balloon shapes can include spherical type shapes that can be useful when drug delivery without mechanical dilation is needed. It is understood that the compliant balloons can be configured to have other shapes and geometries.

Variations of the compliant balloon can generally be low pressure, elastic, and capable of distending significantly (e.g., up to 600%). In some applications, the compliant balloon can be configured to conform to the body cavity in which it is expanded in order to contact a large surface area of the surrounding tissue. The pressure exerted by the compliant balloon when expanded can be sufficient to maintain contact with the tissue, but not cause unwanted damage (e.g., breaking bone, tissue damage) or reshaping (e.g., displacing tissue). To achieve this, the compliant balloon material can be formed of, for example, latex, silicone, polyurethane (PE), polyvinyl chloride (PVC), and/or low durometer Pebax® polyether block amides, and have inflation pressures less than 1 atm, or between about 1 atm and about 2 atm. Higher pressures can be employed when dilation of sinus ostia is intended, for example, inflation pressures ranging from about 6 atm to about 16 atm, or from about 6 atm to about 10 atm. Compliant balloons can be able to conform to irregular geometries in body cavities in order to effectively deliver drugs, for example, in the nasal or sinus cavities, or sinus ostia. For example, a compliant balloon can be used to contact the inferior turbinate for the treatment of allergies. In some variations, the compliant balloons can be molded from suitable materials, e.g., the materials described above. To achieve a low profile delivery configuration, the compliant balloons can be pleated, folded, or wrapped upon themselves.

Alternatively, the expandable member can be a non-compliant balloon. Non-compliant balloons can be made from non-elastic materials having higher durometer such as polyethylene terephthalate (PET), crosslinked polyethylene, and nylon polymers. Non-compliant balloons can have an inflation pressure between 10 atm and 22 atm, between 14 atm and 20 atm, or 20 atm or higher, and can only distend by about 5% to about 7%, or about 5% to about 10%, when inflated. Thus, non-compliant balloons will typically be inflated to an inflation pressure of at least about 10 atm to deliver drug crystals to target tissue, and to higher pressures up to about 25 atm when sinus ostia dilation is desired. The non-compliant balloons can have any suitable shape, e.g., as shown in FIGS. 1A-1N. In some variations, non-compliant balloon shapes can include cylindrical type shapes. It is understood that the non-compliant balloons can be configured to have other shapes and geometries.

The non-compliant balloon can be molded to a desired inflated geometry from non-compliant materials that retain their predetermined size and shape under pressure. To achieve a low profile delivery configuration, the non-compliant balloon can be pleated, folded, or wrapped upon itself. Upon inflation, the balloon can unfurl to expand to the predetermined expanded configuration. The expanded non-compliant balloon can contact a large surface of the surrounding tissue without dilating or damaging the tissue.

In a further variation, the expandable member can be a semi-compliant balloon. Semi-compliant balloons are generally formed by compliant materials but have a higher inflation pressure than compliant balloons. For example, semi-compliant balloons can be made from polyethylene terephthalate (PET), nylon polymers such as nylon 6 (polycaprolactam), or Pebax® polyether block amides (single or dual layer) but have an inflation pressure of 10 atm to 20 atm. Such balloons can be capable of distending about 18% to about 30% upon inflation. Other semi-compliant balloons can allow for about 5% to about 10% distension, and can have an inflation pressure between about 8 atm to 15 atm, more specifically between about 10 atm to 12 atm. Thus, semi-compliant balloons will typically be inflated to an inflation pressure of at least about 8 atm to deliver drug crystals to target tissue, and to higher pressures up to about 20 atm when sinus ostia dilation is desired. Semi-compliant balloons can both distend with inflation and unfurl with inflation. Semi-compliant and non-compliant balloons can be useful when enlargement or dilation of tissue sites, e.g., sinus ostia, is needed.

Semi-compliant balloons can have any suitable shape, e.g., as shown in FIGS. 1A-1N. It is understood that the semi-compliant balloons can be configured to have other shapes and geometries. In some variations, the semi-compliant balloons can be molded from suitable materials, e.g., the materials described above. To achieve a low profile delivery configuration, the semi-compliant balloons can be pleated, folded, or wrapped upon themselves.

Balloon sizes and shapes can be designed for specific anatomies and applications. For example, in some variations, a mushroom-shaped balloon (FIG. 1M) or a dual balloon (FIG. 1N) can be useful when treating Eustachian tube dysfunction or tracheal stenosis. While compliant balloons can conform to the particular geometries of a cavity, the balloon can additionally or alternatively be molded to match the general size and shape of the space. For example, cylindrical compliant balloons having sizes of, for example, 3 mm diameter×20 mm length, can be utilized for Eustachian tube treatment (e.g, to treat the cartilaginous portion of the tube). Spherical non-compliant balloons having a diameter of, for example, about 15 mm to about 50 mm, can be used for treatment of the inferior turbinate. When treatment of the sinus ostium is desired, balloons having a diameter of about 4 mm to about 6 mm, and a length or about 10 mm to about 25 mm, can be employed. Shorter lengths can be utilized for pediatric patients. Molding the size and shape of a non-compliant balloon can require more tailoring to the deployment location (i.e., cavity) so that the balloon can amply contact the surrounding tissue upon inflation (without the ability to conform to the tissue) without dilatation. In some variations, the balloons can have a multi-lobe shape, where the lobes can have the same or different shapes.

Figure 1E:
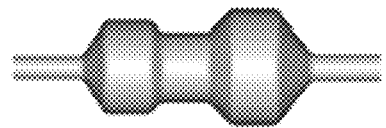
Figure 1C:
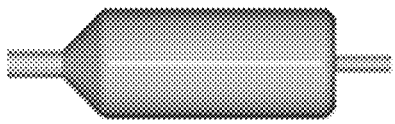
Figure 1F:
Figure 1G:
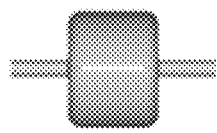
Figure 1J:
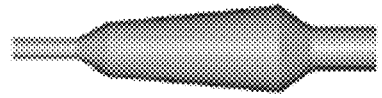
Figure 1H:
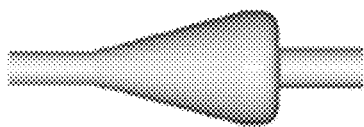
Figure 1K:
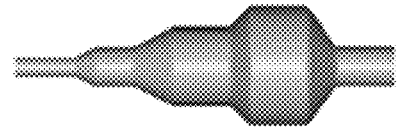
Figure 1I:
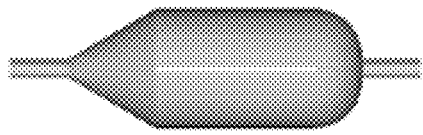
Figure 1L:
Figure 1M:
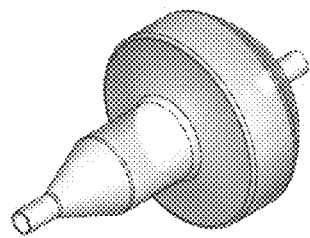
Figure 1N:
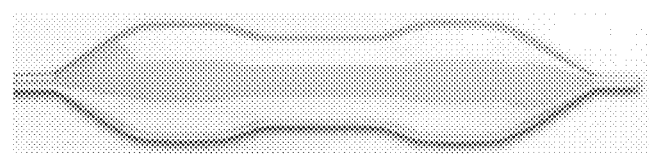

Referring to FIGS. 1A-1N, the compliant, non-compliant, and semi-compliant balloons can be conical (FIG. 1A), tapered (FIG. 1J), spherical (FIG. 1B), square (FIG. 1G), a square with a conical end (FIG. 1H), an elongated square with a conical end (FIG. 1C), an elongated sphere (FIG. 1D), an elongated sphere with a conical end (FIG. 1I), or dogbone shaped (FIG. 1E). Alternatively, the balloons can have a step or multiple steps of varying height (FIG. 1K), or can be configured to expand in a particular direction (FIGS. 1F and 1N). Directionally expanding balloons can be useful e.g., when it is desired to deliver drug to the inferior turbinate but not the nasal septum. Another useful balloon shape can be similar to a star.

Additionally, the balloons can include one or more ports configured for suction, irrigation, deployment of viewing elements (e.g., optic viewers, magnetic imagers, etc.), and/or use with an endoscope or rhinoscope. The balloons can be delivered over a guidewire, with fiberoptic guidance, e.g., using a lighted guide or lighted guidewire, or via a conformable shaft. In some variations, the balloons can be configured to be delivered by a physician using a single hand. In some variations, it can be useful for the balloons to be delivered with the systems described in co-pending U.S. patent application Ser. No. 16/436,363. To achieve a low-profile delivery configuration, the compliant, non-compliant, and semi-compliant balloons can be pleated, folded, or wrapped upon themselves. The number of pleats or folds can vary depending on, for example, the shape of the expandable member, the target tissue to be treated, and/or the intended number of expansions, as previously stated. The pleats or folds can also help with protecting against loss of the drug layer and drug crystals contained therein.

Drug Layer

The expandable members described herein generally include a drug layer at least partially covering their outer surface. The drug layer can include an active agent in crystalline form, amorphous form, or a combination thereof. In addition to the drug, the drug layer can also include an excipient or combination of excipients. Suitable excipients include without limitation, poly(vinyl pyrrolidone), polysorbates, poly(ethylene glycol), propylene glycol, glycerol caproate, and combinations and mixtures thereof. The excipients can be useful in adjusting the rate and/or amount of transfer of the drug layer to the target tissue upon expansion of the expandable member. In one variation, the excipient is a polysorbate, where the polysorbate used can be any one of the polysorbates 20, 21, 40, 60, 61, 65, 80, 81, 85, and 120, or a combination thereof. In another variation, the excipient is poly(ethylene glycol). In a further variation, the excipient is a combination of a polysorbate (e.g., any one of the polysorbates 20, 21, 40, 60, 61, 65, 80, 81, 85, or 120, or a combination thereof) and poly(ethylene glycol). In some variations, the active agent is mometasone furoate at least partially in crystalline form, and the excipient is a combination of a polysorbate (e.g., any one of the polysorbates 20, 21, 40, 60, 61, 65, 80, 81, 85, or 120, or a combination thereof) and poly(ethylene glycol). In variations, the drug layer can include a mixture of mometasone furoate, poly(ethylene glycol), a polysorbate in relative ratios set forth herein. In some further variations, about 60% of the mometasone furoate can be provided in the drug layer in crystalline form.

Figure 4:
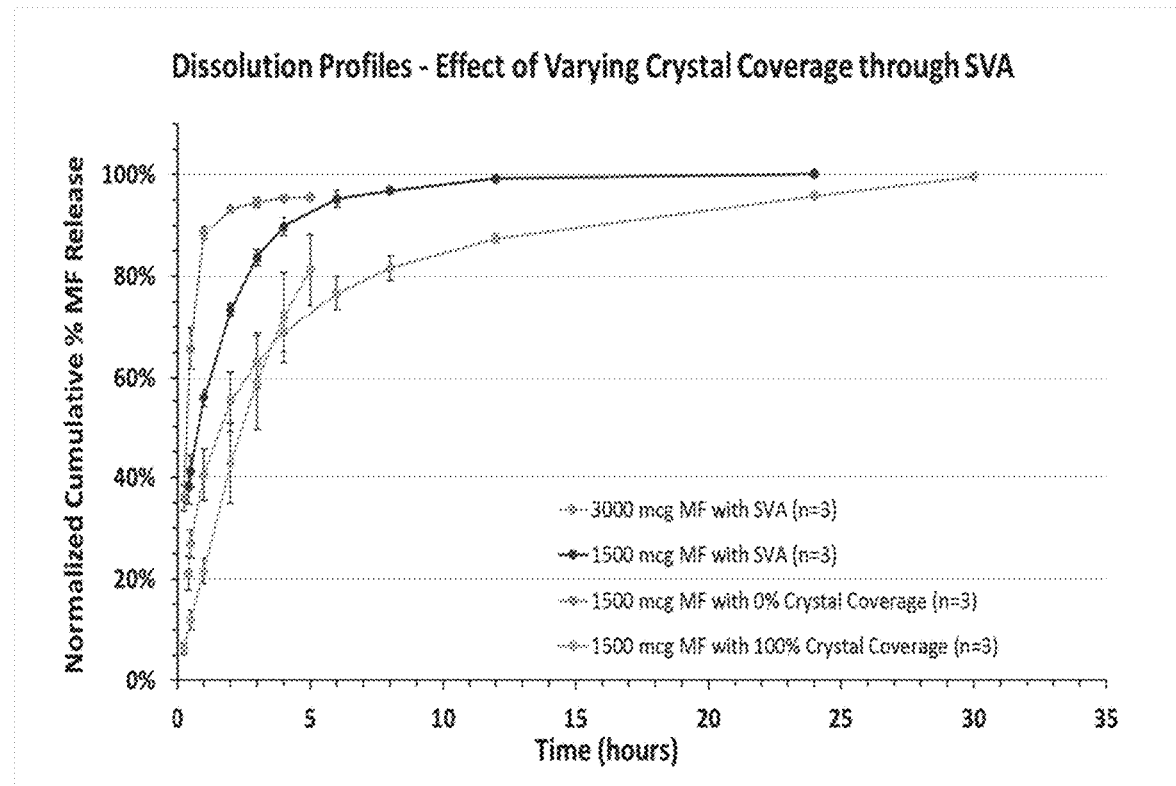
FIG. 4 is a graph comparing the in vitro release rates for expandable members having varying amounts of crystalline mometasone furoate.

The amount of crystalline and amorphous drug provided in the drug layer will generally vary depending on the active agent employed, target tissue being treated, therapeutic drug level desired in the target tissue, and/or the drug release profile desired. For example, the ratio of amorphous to crystalline drug in the drug layer can be about 1:3, 1:2, 1:1, 2:1, or 3:1. A higher amorphous to crystalline drug ratio can lead to quicker tissue absorption due to the higher solubility of amorphous drug. In turn, a higher crystalline to amorphous drug ratio can lead to longer residence time of the drug on tissue. For example, FIG. 4 shows that the in vitro release rate for mometasone furoate (MF) is fastest when the drug layer contains the active agent only in amorphous form (0% crystals), and slowest when the drug layer contains the active agent only as crystals (100% crystals). Thus, a combination of amorphous and crystalline drug in the drug layer can provide immediate release of the active agent to begin treatment of a nose, ear, or throat condition, as well as sustained release of the active agent into the target tissue, as illustrated by the moderate in vitro release rates for drug layers subjected to solvent vapor annealing (SVA) in FIG. 4. In some variations, the drug layer is formed to include about 60% of the active agent as drug crystals. In one variation, the drug layer is formed to include mometasone furoate, where about 60% of the mometasone furoate is in crystalline form. The ratio of crystalline to amorphous drug in the drug layer can be adjusted during the drug layering process onto the expandable member, e.g., during the solvent vapor annealing process, as further described below, or during sterilization.

The size of the drug crystals can also be varied depending on the active agent employed, target tissue being treated, therapeutic drug level desired in the target tissue, and amount of drug crystals present in the drug layer. It can be beneficial to adjust the amount of drug crystals in the drug layer based on the average length of the crystals in order to achieve a therapeutically effective amount of an active agent in the target tissue over a treatment period. In variations where the drug crystals are larger, e.g., having an average length greater than about 80 µm, it can be beneficial for the expandable members to include a drug layer having at least about 60% of the active agent as drug crystals in order to achieve a therapeutically effective amount of the active agent in the target tissue. In variations where the drug crystals are smaller, e.g., having an average length less than about 80 µm, therapeutic levels of an active agent in a target tissue can be achieved using expandable members including a drug layer having less than about 60% of the active agent as drug crystals. Therapeutically effective amounts will vary based upon the particular active agent being delivered. In the case of mometasone furoate, a therapeutically effective amount is generally a mometasone furoate concentration in tissue of at least 0.1 µg/gm.

More specifically, when the drug layer comprises at least about 60% of the active agent as drug crystals, the drug crystals have an average length greater than about 80 µm, greater than about 90 µm, greater than about 100 µm, greater than about 110 µm, greater than about 120 µm, or greater than about 130 µm. When the drug crystals have an average length of about 130 µm, it can be beneficial for the drug layer to comprise at least about 65% of the active agent as drug crystals.

Furthermore, when the drug layer comprises drug crystals having an average length of less than about 80 µm, the drug layer can comprise less than about 60%, less than about 55%, less than about 50%, less than about 45%, less than about 40%, less than about 35%, less than about 30%, less than about 25%, or less than about 20% of the active agent as drug crystals.

For example, as shown in TABLE 1, expandable members (expandable balloons) including drug layers with at least about 60% mometasone furoate (MF) crystals sized greater than about 80 µm were able to achieve 30 day tissue concentrations (in sheep frontal sinus ostia) of at least 0.1 µg/gm. Balloons including smaller crystals, e.g., those sized less than 80 µm, were able to achieve high mometasone furoate concentrations in tissue (about 5.0 µg/gm) at 30 days with less than 60% of the drug layer containing drug crystals. The amount of mometasone furoate transferred to the ostia (total MF released) was measured after inflation of balloons having a drug layer including the listed dose of mometasone furoate drug crystals and poly(ethylene glycol) and polysorbate as the excipients.

TABLE 1

| Dose (µg) | % Drug Crystals | Crystal Size (µm) | Total MF Released (µg) | Average 30 day tissue MF Concentration in Sinus Ostia (µg/gm) |
| --- | --- | --- | --- | --- |
| 1500 | 36.4 | 78.7 | 350 | 5.0 |
|  | 62.5 | 128.1 | 478 | 1.0 |
| 3000 | 60.4 | 91.1 | 1778 | 0.1 |
|  | 67.4 | 132.6 | 1058 | 2.0 |

The drug layer can cover the entire expandable member or a portion thereof, as previously stated. For example, the drug layer can be patterned on the expandable member or provided on specific areas of the expandable member, depending on, e.g., the anatomy to be treated. For example, the pattern could include solid or dashed lines of the drug layer, the drug layer dotted on the expandable member, or the drug layer provided as a spiral around the expandable member, etc. In some variation, the drug layer can be provided within the apices of the pleats or folds of the expandable member. The thickness of the drug layer can range from about 10 µm to about 500 µm. In some variations, the thickness of the drug layer can be varied, e.g., structured to be thicker on some areas of the expandable member than others. In other variations, the thickness of the drug layer is formed so that the active agent can be delivered over multiple expansions, where a portion of the drug layer is delivered with each expansion. The drug layer can be formulated to have a similar compliance as the expandable member, with an appropriate ductility to prevent breaking and flaking upon distension or unfolding of the expandable member. In addition to the drug, the drug layer formulation can include other compounds or additives, such as excipients, binding agents, plasticizers, solvents, surfactants, chelators, penetration enhancers, mucoadhesives, mucolytics, and the like. When the site to be treated includes mucosal or mucociliary tissue, it can be useful for the drug layer to include excipients such as a penetration enhancer, a mucoadhesive and/or a mucolytic to enhance drug delivery across the mucus layer. In some variations, excipients having a molecular weight of 1000 Da or less can be beneficial in enhancing drug uptake through mucosal tissue.

Another layer (e.g., a topcoat) can be applied on the drug layer to protect it prior to deployment of the expandable member or to facilitate release of the drug (e.g., by priming the surface of the expandable member with a hydrophilic priming agent, or by including a hydrophilic priming agent in the topcoat). The topcoat can lack an active agent, but in some instances it can include small amounts of one or more active agents. In some variations, the topcoat is configured to dissolve or degrade upon contact with the target tissue site but before the expandable member is expanded.

The drug layer formulation can comprise an excipient to plasticize the coating and/or enhance film integrity. An optional plasticizer can be added to increase ductility and integrity of the coating. Examples of plasticizers can include low molecular weight poly(ethylene glycol), glycerol, polysorbates, fatty acids, sebacates, fatty alcohols, lipids, lecithin, oils such as vegetable oils, glycol esters, propylene glycol, and castor oil. When a plasticizer is employed, the ratio of drug, excipient, and plasticizer in the coating can range from about 0.5:1:0.1, respectively to 10:1:1, respectively. In some variations, the ratio of drug, excipient, and plasticizer can range from 2:1:0.1, respectively to 3:1:0.5, respectively.

An excipient or polymer can be added to the drug layer formulation to enhance film forming and coating integrity. These materials can be natural or synthetic. Natural polymers can include chitosan, collagen, elastin, silk, silk-elastin, alginate, cellulose, dextran, polyalkoanates, hyaluronic acid, gelatin, and gellan. Synthetic bioresorbable polymers can include polylactide (PLA), poly(lactide-co-glycolide), poly(L-lactide-co-ε-ca-prolactone), polyglycolide, polyhydroxybutyrate, polyhydroxyvalerate, poly(ethylene glycol) (PEG), polydioxanone, polyglactin, poly(ε-caprolactone), polyglyconate, poly(glycolide-co-trimethylene carbonate), poly(sebacic acid), poly(ester urethane) and poly(ester urethane) urea.

When poly(ethylene glycol) (PEG) is used, its molecular weight can be adjusted to improve layering properties. In general, the molecular weight of PEG that can be used ranges from about 0.2 kDa to about 10 kDa (in other words, varieties of PEG ranging from PEG 200 to PEG 1000). In some specific variations, the PEG used can be PEG 600, PEG 800, PEG 1000, PEG 1500, PEG 2000, PEG 3000, PEG 3350, PEG 4000, PEG 6000, or PEG 8000. In some variations, a relatively low molecular weight PEG (e.g., less than about 1.2 kDa) can enhance the rate of drug release and mucosal tissue uptake. In other variations, PEG having a molecular weight more than about 1.2 kDa can slow the drug release rate over multiple inflations or delay mucosal tissue uptake. For some implementations, a relatively high molecular weight PEG can also be employed, e.g., PEG having a molecular weight of 6 kDa. Alternatively, the drug layer can include layers of PEG having different molecular weights. For example, layers could alternately include high and low molecular weight PEG when multiple inflations are being contemplated.

Cross-linked versions of synthetic layering excipients can also be used and include without limitation, crosslinked PEG, polyNIPAAM, PEG-PLA block copolymers, and thermally cross-linked polaxamers (e.g., Pluronics). Crosslinked PEGs can consist of pre-reacted reactive PEGs such as mixtures of reactive multi-arm PEG succinimydyl succinate and multi-arm PEG amine. Either 4-arm PEG or 8-arm PEG can be utilized to control the crosslink density and swell ratio. Other multi-arm PEG-NETS (N-hydroxylsuccinimide) esters such as PEG succinimidyl glutarate can be used. Cellulosics can also be added to the coating formulation.

The formulation can also comprise an excipient for enhancing or slowing drug layer transfer, enhancing or slowing drug release from the coating, and/or enhancing adhesion to tissue. Particular combinations of excipients and drugs can help to allow the coating to be released from the outer membrane of the expandable member and to adhere to mucus and/or mucosal tissue. Excipients having mucoadhesive properties can be useful and include without limitation, chitosan, polyacrylic acid, polyglutamic acid, carboxymethylcellulose, sodium hyaluronate, and sodium alginate. In some variations, the coating is formulated to be hydrophobic to prevent washout during procedures where tissue sites undergo irrigation.

Specifically, in some instances, it can be desirable for the drug to excipient ratio to be high to enhance fast release of drug from the expandable member during a short time period of inflation. Examples include drug to excipient ratios of 1:3 or higher, or 1:1 or higher. In some instances, moisture and/or mucous from the body cavity after delivery can soften the drug layer and help to allow the drug layer to be transferred to tissue. In other instances, the excipient can be amphiphilic (i.e., possess both hydrophilic and lipophilic properties) to promote hydrophilic release from the expandable member when moist and lipophilic interaction with the drug. Examples of amphiphilic polymers and excipients can include poly(ethylene glycol), poly(vinyl pyrrolidone), phospholipids, fatty acids, sodium dodecyl sulfate, polysorbates, poloxamers, hydroxypropyl-beta-cyclodextrin, and sucrose fatty acid monoester.

Alternatively, the drug to excipient ratio can be adjusted to retard or slow the release of drug to a tissue site. Here relatively higher lipophilic drug to hydrophilic excipient ratios, e.g., ratios of 1:1, 2:1, or 3:1, can be used to slow dissolution of the drug, and thus slow release. These ratios can be useful when a single expandable member will be used to treat multiple sites and/or undergo multiple expansions.

Additionally or alternatively, the drug itself can be lipophilic. In these variations, if the expanded expandable member presses against and conforms to the tissue at the treatment site, the lipophilic nature of the drug(s) contained in the coating on the outside surface of the expandable member can promote transfer to and absorption by the tissue. Moisture within the body cavity (e.g., the sinus, Eustachian tube and other applicable bodily structures described herein) can facilitate this transfer. Other factors that can affect drug/drug layer transfer from the expandable member (e.g., the balloon) include the amount of contact pressure exerted by the expandable member, the amount of contact of the expandable member to the tissue site, and the amount of injury to the surface of the tissue site. The physician can also irrigate the tissue and/or expandable member prior to device deployment to enhance drug release from the expandable member.

As previously mentioned, once the drug layer is transferred to tissue, e.g., mucosal tissue, within a body cavity, it can act as an in situ depot that enables maintenance of a therapeutic local level of drug for a desired time frame. In some instances, the drug layer containing the one or more drugs can be at least partially biodegradable and/or biosoluble. As the drug and/or drug layer degrades and/or dissolves over the course of the desired time frame, the drugs can be released to the target tissue and to the anatomies distal to the target tissue. In some variations, the use of cross-linked excipients can help maintain the drug at the target tissue site for the desired time frame. In other variations, the inclusion of high molecular weight excipients in the drug layer can enhance residence time of the drug at the target tissue site. In yet further variations, incorporating the crystal form of the drug in the drug layer can help to increase the efficiency of drug delivery and/or sustained release of the drug at the target tissue site. When treating the paranasal sinuses, it can be beneficial for the drug layer to comprise at least about 60% of the active agent as mometasone furoate drug crystals, a polysorbate, and poly(ethylene glycol). Such a drug layer can be formed at ratios of the drug and excipients as set forth herein.

In some instances, use of a non-compliant or semi-compliant balloon (versus a compliant balloon) can increase the efficiency of drug uptake at a mucosal tissue site. This is because the higher pressures required to inflate the balloons can displace the mucous layer and also lead to epithelial tissue injury, which in turn can enhance drug delivery into the tissue. Tissue injury can also be induced by employing a balloon having spikes or a rough surface molded or adhered thereto, or a balloon capable of scoring, cutting, and/or tearing tissue.

In other instances, use of a mucoadhesive excipient can increase the efficiency of drug delivery at the tissue site. Exemplary mucoadhesive excipients include without limitation, carbomers, glyceryl monooleate, hypromellose, oleic acid, polycarbophil, polyethylene oxide, poly(ethylene glycol), and sodium alginate. Other mucoadhesives could obtain their adhesive properties by wetting of a soluble coating or polymer, charge adhesion (e.g., of anionic polymers such as polyacrylic acid, cellulosics, chitosan, gellan, carbopol, etc.), and covalent adhesion with e.g., a protein reactive gel such as PEG-NETS. In one variation, the mucoadhesive is poly(ethylene glycol).

Penetration enhancers can also be included in the drug layer formulation to enhance drug delivery through, e.g., the mucous layer, and to the target tissue. Exemplary penetration enhancers include, but are not limited to, dimethyl sulfoxide, glyceryl monooleate, glycofurol, isopropyl myristate, isopropyl palmitate, lanolin, light mineral oil, linoleic acid, menthol, myristic acid, myristyl alcohol, oleic acid, oleyl alcohol, palmitic acid, polyoxyethylene alkyl ethers, polyoxylglycerides, pyrrolidone, sodium lauryl sulfate, thymol, tricaprylin, triolein, and combinations and mixtures thereof.

The expandable member can comprise any suitable drug or agent, depending on the desired use thereof. The drug or active agent can comprise at least one of a diagnostic agent or a therapeutic agent, for example. Suitable classes of drugs include, for example, local anesthetics, painkillers, vasoconstrictors, antiseptics, antioxidants, anti-inflammatory agents, anti-allergens, anti-cholinergic agents, antihistamines, anti-infectives, anti-platelet agents, anti-coagulants, anti-thrombotic agents, anti-scarring agents, anti-proliferative agents, chemotherapeutic agents, anti-neoplastic agents, decongestants, healing promoting agents and vitamins (for example, retinoic acid, vitamin A, depaxapanthenol, vitamin B and their derivatives), hypersomolar agents, immunomodulators, immunosuppressive agents, mucolytics, and combinations and mixtures thereof.

The drug coated expandable members, e.g., drug coated balloons, can be used to treat patients that have had prior surgery such as functional endoscopic sinus surgery (FESS) or sinus balloon dilation without delivery of a drug by the balloon, or patients that have not had prior surgery. For the treatment of nasal conditions, it can be useful for the drug to comprise an anti-inflammatory agent, an anti-infective agent, an antihistamine, a decongestant, a mucolytic agent, or combinations or mixtures thereof. The balloon for use in the nose, e.g., in the paranasal sinuses can be shaped as a long spherical balloon (e.g., see FIG. 1D). For the treatment of otic conditions, it can be useful for the drug to comprise an anti-inflammatory agent, an anti-infective agent, or combinations or mixtures thereof. The balloon for use in the ear can have a mushroom shape (e.g., see FIG. 1M) or a dual balloon shape (see, e.g., FIG. 1N). For the treatment of throat conditions, it can be useful for the drug to comprise a painkiller, an anti-infective agent, a chemotherapeutic agent, or combinations or mixtures thereof. The balloon for use in the throat can be a long spherical balloon having a larger diameter and longer length than that used in the sinus. For example, the balloon can have a diameter of about 16 mm and a length of about 40 mm.

In some variations, a mucolytic agent is included in the drug layer to help clear the mucous layer, as previously stated. The mucolytic agent can comprise carbocysteine, erdosteine, acetylcysteine, bromheksin, expigen syrup (sorbimacrogol laurate 300 and ammonium chloride), guaifenesin, glyceryl guaicolate, iodinated glycerol, or combinations or mixtures thereof.

Examples of antioxidants include tocopherol (vitamin E), alpha tocopherol, ascorbic acid, ascorbyl palmitate, butylated hydroxyanisole, butylated hydroxytoluene, citric acid monohydrate, erythorbic acid, ethyl oleate, fumaric acid, malic acid, methionine, monothioglyceraol, phosphoric acid, potassium metabisulfite, proprionic acid, propyl gallate, sodium ascorbate, sodium thiosulfate, sulfur dioxide, citric acid monohydrate, tartaric acid, and thymol.

Examples of local anesthetics include ropivicaine, mepivicaine, cocaine, procaine, lidocaine, hydrocodone, oxycodone and fentanyl, morphine. Examples of vasoconstrictors include epinephrine, levonordefrin, and adrenaline.

Anti-infective agents generally include antibacterial agents, antifungal agents, antiparasitic agents, antiviral agents, antiseptics, iodine (e.g., povidone-iodine), potassium sorbate, sorbic acid, thimersol, thymol, butylene glycol, coconut oil, and vanillin. Anti-inflammatory agents generally include steroidal and nonsteroidal anti-inflammatory agents.

Examples of anti-allergic agents that can suitable for use with the described methods and devices include, but are not limited to, pemirolast potassium (ALAMAST®, Santen, Inc.), and any prodrugs, metabolites, analogs, homologues, congeners, derivatives, salts and combinations thereof. Examples of antiproliferative agents include, but are not limited to, sirolimus, everolimus, temsirolimus, actinomycin D, actinomycin IV, actinomycin I1, actinomycin X1, actinomycin C1, and dactinomycin (COSMEGEN®, Merck & Co., Inc.). Examples of antiplatelet, anticoagulant, antifibrin, and antithrombin agents include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibodies, recombinant hirudin, and thrombin inhibitors (ANGIOMAX®, Biogen, Inc.), and any prodrugs, metabolites, analogs, homologues, congeners, derivatives, salts and combinations thereof. Examples of pro-healing agents include, but are not limited to, vitamin A.

Examples of cytostatic or antiproliferative agents that can be suitable for uses with the described methods and devices include, but are not limited to, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof.

Examples of antibacterial agents that can be suitable for use with the described methods and devices include, but are not limited to, aminoglycosides, amphenicols, ansamycins, betalactams, β-lactams such as penicillins, lincosamides, macrolides, nitrofurans, quinolones, sulfonamides, sulfones, tetracyclines, vancomycin, and any of their derivatives, or combinations thereof. Examples of penicillins that can be suitable for use with the described methods and devices include, but are not limited to, amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, and ticarcillin. In one variation, the antibacterial agent comprises ciprofloxacin. In another variation, the antibacterial agent comprises amoxicillin.

Examples of antifungal agents suitable for use with the described methods and devices include, but are not limited to, allylamines, imidazoles, polyenes, thiocarbamates, triazoles, and any of their derivatives. Antiparasitic agents that can be employed include, but are not limited to, atovaquone, clindamycin, dapsone, iodoquinol, metronidazole, pentamidine, primaquine, pyrimethamine, sulfadiazine, trimethoprim/sulfamethoxazole, trimetrexate, and combinations thereof.

Examples of antiviral agents suitable for use with the described methods and devices include, but are not limited to, acyclovir, famciclovir, valacyclovir, edoxudine, ganciclovir, foscamet, cidovir (vistide), vitrasert, formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomethoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92-938X (1-beta-D-ribofuranosylpyrazole-3,4-dicarboxamide), LY253963 (1,3,4-thiadiazol-2-yl-cyanamide), RD3-0028 (1,4-dihydro-2,3-Benzodithiin), CL387626 (4,4'-bis[4,6-d] [3-aminophenyl-N,N-bis(2-carbamoylethyl)-sulfonilimino]-1,3,5-triazin-2-ylamino-biphenyl-2,2'-disulfonic acid disodium salt), BABIM (Bis[5-Amidino-2-benzimidazoly-1]-methane), NIH351, and combinations thereof.

Examples of antiseptic agents suitable for use with the described methods and devices include, but are not limited to, alcohol, chlorhexidrine, iodine, triclosan, hexachlorophene, and silver-based agents, for example, silver chloride, silver oxide, and silver nanoparticles.

Anti-inflammatory agents can include steroidal and nonsteroidal anti-inflammatory agents. Examples of suitable steroidal anti-inflammatory agents include, but are not limited to, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, any of their derivatives, and combinations thereof. In some variations, a corticosteroid is used in the sinuses and other bodily structures described herein to prevent or reduce inflammation post-surgery. The corticosteroid will generally be one with high potency, high binding to glucocorticoid receptors, and low bioavailability. For example, in some variations the corticosteroid comprises mometasone furoate, or a pharmaceutically acceptable salt, solvate, hydrate, ester, free base, enantiomer, racemate, polymorph, amorphous, or crystal form thereof. In other variations, the corticosteroid comprises dexamethasone, or a pharmaceutically acceptable salt, solvate, hydrate, ester, free base, enantiomer, racemate, polymorph, amorphous, or crystal form thereof.

Examples of suitable nonsteroidal anti-inflammatory agents include, but are not limited to, COX inhibitors. These COX inhibitors can include COX-1 or COX nonspecific inhibitors such as, for example, salicylic acid and derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, diclofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone. The COX inhibitors can also include selective COX-2 inhibitors such as, for example, diaryl-substituted furanones such as rofecoxib; diaryl-substituted pyrazoles such as celecoxib; indole acetic acids such as etodolac and sulfonanilides such as nimesulide).

Examples of chemotherapeutic/antineoplastic agents that can be used in the devices described here include, but are not limited to antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites or other agents that block cancer cell growth by interfering with certain cell functions, usually DNA synthesis (e.g., 6-mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin), plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase inhibitors such as aminoglutethimide and formestane, triazole inhibitors such as letrozole and anastrazole, steroidal inhibitors such as exemestane), antiangiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, AE-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000), which is expressly incorporated herein by reference, biological response modifiers (e.g., interferon, bacillus calmette-guerin (BCG), monoclonal antibodies, interleukin 2, granulocyte colony stimulating factor (GCSF), etc.), PGDF receptor antagonists, herceptin, asparaginase, busulphan, carboplatin, cisplatin, carmustine, chlorambucil, cytarabine, dacarbazine, etoposide, flucarbazone, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol or paclitaxel, taxotere, azathioprine, docetaxel analogs/congeners, derivatives of such compounds, and combinations thereof.

Examples of decongestants that can be used in the devices and methods described here include, but are not limited to, epinephrine, pseudoephedrine, oxymetazoline, phenylephrine, tetrahydrozolidine, and xylometazoline. Examples of mucolytics that can be used in the devices and methods described here include, but are not limited to, acetylcysteine, dornase alpha, and guaifenesin. Anti-histamines such as azelastine, diphenhydramine, and loratidine can also be used in the systems and methods described herein.

Suitable hyperosmolar agents that can be used in the devices described here include, but are not limited to, furosemide, sodium chloride gel, and other salt preparations that draw water from tissue or substances that directly or indirectly change the osmolarity of the mucous layer.

Other bioactive agents useful in the present invention include, but are not limited to, free radical scavengers; nitric oxide donors; rapamycin; methyl rapamycin; everolimus; tacrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells including, but not limited to prokaryotes and eukaryotes such as, for example, epithelial cells and genetically engineered epithelial cells; dexamethasone; botulinum toxin and other neurotoxins; and, any prodrugs, metabolites, analogs, homologues, congeners, derivatives, salts and combinations thereof.

Examples of free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate, and any analogs, homologues, congeners, derivatives, salts and combinations thereof.

The selection of drug type, drug form (e.g., crystal and amorphous), timing of delivery, and drug dose can be determined by the intended treatment plan, and can be further fine-tuned to meet the specific needs of an individual patient. Components of the drug layer can be altered to adjust the release rates of the drug and/or the transfer rate of the coating to tissue. The drug layer can be formulated so that at least 25%, at least 40%, at least 50%, at least 60% at least 70%, at least 80%, or at least 90% of the drug layer is transferred to tissue upon expansion of the expandable member. In one variation, at least 80% of the drug layer is transferred upon expansion of the expandable member.

The desired amount of drug layer or drug crystal transfer can be accomplished with one or multiple expansions of the expandable member. In some variations, the expandable member can be structured so that drug crystals are delivered to target tissues with one, two, three, four, five, six, seven, or eight expansions. For example, when multiple expansions are performed with a single device, the drug crystals can be formulated to be partially transferred with each expansion. This can be useful when a single device is to be used to treat multiple tissue sites, e.g., multiple paranasal sinuses. Partial transfer of the drug crystals can be accomplished by partially transferring the drug layer to target tissue with each expansion. For example, when the drug layer comprises multiple sub-layers, each sub-layer can be transferred with every expansion. In other variations, the inflation pressure can be adjusted with each expansion to effect partial transfer of the drug layer with each expansion, e.g., inflation pressure can be increased with each expansion. The amount of drug layer or drug crystal transfer can also be adjusted by using a different number of pleats or folds in the balloon.

In some variations, the drug layer or drug crystals can be formulated so that their transfer is linear with each expansion, e.g., with each balloon inflation. For example, 25% of the drug crystals can be transferred with the first inflation, another 25% can be transferred with the second inflation, another 25% transferred with the third inflation, and the remaining 25% transferred with the fourth inflation. In other variations, the drug crystals can be formulated to have a first order type of transfer. Broadly, the drug crystals and drug layer can be formed and formulated to have a first order transfer profile where 40%±30% of the crystals are transferred with a first inflation, 30%±20% of the crystals are transferred with a second inflation, 20±10% are transferred with a third inflation, and 10%±5% are transferred with a fourth inflation. In one example, about 60% of the crystals are transferred with the first inflation, about 20% of the crystals are transferred with the second inflation, about 10% are transferred with the third inflation, and about 5% are transferred with the fourth inflation. In another example, about 60% of the crystals are transferred with the first inflation and about 40% of the crystals are transferred with the second inflation. In a further example, about 50% of the crystals are transferred with the first inflation, about 20% of the crystals are transferred with the second inflation, about 10% are transferred with the third inflation. Furthermore, the drug layer or drug crystals can be formulated so that the total amount of drug transfer after the target number of expansions against tissue (e.g. after one, two, three, four, five, or six expansions) is about 96% or more of the initial drug loaded onto the expandable member. In specific implementations, about 4% or less of the initial drug load will remain on the expandable member after four inflations delivering drug to one or more target tissues. In some instances, it can be beneficial to treat the target tissue with two expansions of the expandable member. Treatment with two expansions can be sufficient to obtain therapeutic levels of the active agent in certain target tissues, as further described in Example 3.

The type of transfer desired can be obtained by altering the structure of the drug layer, altering components of the drug layer formulation and/or their amounts therein, and/or altering various steps of the drug layer manufacturing process. For example, when linear transfer is desired, the drug layer can be provided in multiple layers on the expandable member, and one layer can be transferred with each expansion. Accordingly, the number of layers will generally correspond to the number of expansions intended to be employed. In some cases, a primer coating without drug can be incorporated between each drug layer. In other instances, a longer inflation time can result in the drug layer exhibiting a first order type of release over multiple expansions.

The surface of the expandable member can be treated prior to layering in a manner that enhances transfer of the drug layer or slows transfer of the drug layer during expansion. For example, when the surface of an inflatable balloon is plasma treated or coated with a primer coating(s), certain parameters of the treatment can be altered to manipulate transfer rates.

The dose of drug (e.g., mometasone furoate) delivered when the drug layer is transferred with any single inflation of the expandable member can range from about 0.1 mg (100 µg) to about 20 mg (20,000 µg). For example, the dose of drug transferred can be about 0.1 mg (100 µg), about 0.2 mg (200 µg), about 0.3 mg (300 µg), about 0.4 mg (400 µg), about 0.5 mg (500 µg), about 1.0 mg (1,000 µg), about 2.0 mg (2,000 µg), about 3.0 mg (3,000 µg), about 4.0 mg (4,000 µg), about 5.0 mg (5,000 µg), about 6.0 mg (6,000 µg), about 7.0 mg (7,000 µg), about 8.0 mg (8,000 µg), about 9.0 mg (9,000 µg), about 10 mg (10,000 µg), about 11 mg (11,000 µg), about 12 mg (12,000 µg), about 13 mg (13,000 µg), about 14 mg (14,000 µg), about 15 mg (15,000 µg), about 16 mg (16,000 µg), about 17 mg (17,000 µg), about 18 mg (18,000 µg), about 19 mg (19,000 µg), or about 20 mg (20,000 µg).

In some variations, the total amount of dose transferred ranges from about 0.1 mg (100 µg) to about 1.5 mg (1,500 µg). In other variations, the total amount of drug dose transferred is up to about 3.0 mg (3,000 µg). In further variations, the total amount of drug dose transferred is up to about 6.0 mg (6,000 µg). The dose density can be configured in view of the size of the expandable device being coated as well as in view of the target tissue to which drug is delivered, for example a balloon designed for tracheal stenosis can have a drug dose of up to about 45.0 mg or greater in order to account for the necessary surface area of the expandable member. The dose density (i.e., the amount of drug per balloon working length surface area) in the coating (e.g., mometasone furoate) can also be adjusted to vary the amount of drug delivered to tissue, and can range from about 5 µg/mm$^2$ to about 600 µg/mm$^2$. For example, the dose density can be 5 µg/mm$^2$, 6 µg/mm$^2$, 7 µg/mm$^2$, 8 µg/mm$^2$, 9 µg/mm$^2$, 10 µg/mm$^2$, 20 µg/mm$^2$, 20 µg/mm$^2$, 30 µg/mm$^2$, 40 µg/mm$^2$, 50 µg/mm$^2$, 60 µg/mm$^2$, 70 µg/mm$^2$, 80 µg/mm$^2$, 90 µg/mm$^2$, 100 µg/mm$^2$, 200 µg/mm$^2$, 300 µg/mm$^2$, 400 µg/mm$^2$, 500 µg/mm$^2$, or 600 µg/mm$^2$. In some variations, e.g., when the coating is provided on a balloon of 6 mm diameter×20 mm length, it can be useful for the coating to include a dose density of mometasone furoate of between about 1 µg/mm$^2$ to about 10 µg/mm$^2$, or between about 4 µg/mm$^2$ (1500 µg) to about 8 µg/mm$^2$ (3000 µg).

The profile of drug delivery can also be tailored or customized by adjusting the amount of drug in the drug layer, the amount of amorphous or crystalline drug in the drug layer, the size of crystals of drug in the drug layer, the distribution or density of crystals of drug in the drug layer, the amount of excipient(s) and/or other component of the drug layer formulation, shape of the expandable member, etc. As previously stated, drug delivery can be linear across each expansion (e.g., 25% of the drug dose delivered to each of four sinuses), first order across each expansion (e.g., 50% of the drug dose delivered with the first expansion, 25% delivered with the second expansion, 15% delivered with the third expansion, and 10% delivered with the fourth expansion), or second order, as desired.

The drug layer can include any suitable number or combination of drugs and excipients, depending on the condition to be treated, desired rate of drug release and coating transfer, etc. The drug layer can include one, two, three, four, or five drugs, or more than five drugs. When two drugs are included in the drug layer formulation, they can be mometasone furoate and an antihistamine, or mometasone furoate and an antibacterial agent. Likewise, the drug layer can include one, two, three, four, or five excipients, or more than five excipients. When the tissue to be treated includes mucociliary tissue, it can be beneficial for the drug layer to include one or more penetration enhancing, mucoadhesive, or mucolytic excipients, as previously stated. For example, the drug layer can include mometasone furoate as the drug, polysorbate as the penetration enhancer, polyacrylic acid as the mucoadhesive, and acetylcysteine as the mucolytic. The drug layer can comprise a drug to excipient ratio ranging from about 3:1 to about 1:3.

In one variation, the drug layer formulation comprises a corticosteroid and a mucoadhesive excipient. In another variation, the drug layer formulation comprises a corticosteroid and a mucolytic excipient. In yet a further variation, the drug layer formulation comprises a corticosteroid and a penetration enhancer as the excipient. The drug layer formulation can also include a corticosteroid, a mucoadhesive excipient, and a mucolytic excipient; or a corticosteroid, a mucoadhesive excipient, a mucolytic excipient, and a penetration enhancer. The corticosteroid in the aforementioned drug layers can be mometasone furoate. Other drug layer formulations can include an antibacterial agent in combination with one or more of a mucoadhesive excipient, a mucolytic excipient, and a penetration enhancer. In some instances, the mucolytic can be the active drug instead of the excipient in the drug layer.

The drug layer formulation can comprise mometasone furoate as the active agent, and as excipients, poly(vinyl pyrrolidone) and a polysorbate. This drug layer variation can be useful in treating a nasal condition, e.g., rhinitis, sinusitis, polypoid edema, or mucosal inflammation. Other drug layers for treating nasal conditions can include mometasone furoate, poly(vinyl pyrrolidone), a polysorbate, and poly(ethylene glycol). Alternatively, the drug layers for treating a nasal condition can include mometasone furoate as the active agent, and as excipients, poly(ethylene glycol) and a polysorbate. Broadly, the drug layers can include mometasone furoate, an excipient, and a polysorbate in a ratio by weight of about [0.5-10.0]:[1.0]:[0.1-1.0]. Examples of these ratios are seen in TABLE 2 below. In further variations, the drug layers for treating a nasal condition can include mometasone furoate as the active agent, and as excipients, poly(vinyl pyrrolidone) and propylene glycol. Other excipient combinations that can be included with mometasone furoate as the active agent are: poly(vinyl pyrrolidone) and a polysorbate; poly(ethylene glycol) and propylene glycol; and poly(ethylene glycol) and glycerol caproate.

In some variations, the coating for treating a nasal condition comprises an antibacterial as the active agent, e.g., amoxicillin, and a polysorbate as the excipient. In other variations, the coating for treating a nasal condition comprises an antibacterial as the active agent, e.g., amoxicillin, and poly(vinyl pyrrolidone) as the excipient. In yet further variations, the coating for treating a nasal condition comprises an antibacterial as the active agent, e.g., amoxicillin, and poly(ethylene glycol) as the excipient. Alternatively, the coating for treating nasal conditions can include an antibacterial as the active agent, e.g., amoxicillin, and a combination of a polysorbate, poly(vinyl pyrrolidone), and poly(ethylene glycol) as excipients.

When the nasal condition involves treating the inferior turbinate, the drug layer can be layered onto a non-compliant spherical balloon having a diameter of, e.g., 15 mm to about 50 mm, and the balloon inflated for a time period of about 5 seconds. When the nasal condition involves treating one or more the sinus ostia, the drug layer can be placed on a cylindrical balloon (either compliant, non-compliant, or semi-compliant) having a diameter of, e.g., about 4 mm to about 6 mm, and a length of about 10 mm to about 25 mm. Here the balloon can also be inflated for a time period of about 5 seconds to about 5 minutes. A single balloon can be inflated multiple times at the same of different target tissue site (e.g., the inferior turbinate or one or more sinus ostia), as previously stated.

When an otic condition is to be treated, the drug layer formulation can include an antibacterial agent, an anti-inflammatory agent, e.g., a corticosteroid such as dexamethasone, or combinations thereof, in addition to an excipient or combination of excipients. For example, the antibacterial agent can comprise ciprofloxacin or amoxicillin, and the excipient can comprise a polysorbate, poly(vinyl pyrrolidone), or poly(ethylene glycol). In one variation, the drug layer formulation comprises ciprofloxacin as the antibacterial, and a polysorbate as the excipient. In another variation, the drug layer formulation comprises ciprofloxacin as the antibacterial, and poly(vinyl pyrrolidone) as the excipient. In yet further variations, the drug layer formulation comprises ciprofloxacin as the antibacterial agent, and poly(ethylene glycol) as the excipient. In some instances, it can useful for the drug layer formulation to include ciprofloxacin and a polysorbate, poly(vinyl pyrrolidone), and poly(ethylene glycol) as excipients.

When the otic condition involves treating the external ear or Eustachian tube, the drug layer can be layered onto a cylindrical compliant balloon having dimensions of, e.g., 3 mm diameter×20 mm length. Here the balloon can be inflated for a time period of about 5 seconds to about 5 minutes. In some instances, a coated non-compliant or semi-compliant balloon can be useful in treating otic conditions. In other variations, treatment of the Eustachian tube can include entirely coating a 6 mm diameter×20 mm length balloon with a drug layer formulation containing mometasone furoate, PEG, and a polysorbate. The coating formulation can include mometasone furoate at 1500 μg or 3000 μg. The balloon can be inflated and then immediately deflated, or inflated for a time period ranging from about 5 seconds to about two minutes. In some variations, the balloon for treating the external ear or the Eustachian tube can be conically shaped (FIG. 1H), tapered (FIG. 1J), or a stepped shape (FIG. 1K).

When a throat condition is to be treated, the drug layer formulation can include as the active agent, a painkiller, an anesthetic, an anti-inflammatory agent, e.g., a corticosteroid, and combinations thereof. Here the drug layer can be provided on a compliant, non-compliant, or semi-compliant balloon depending on the specific throat condition being treated, and the balloon inflated for about 5 seconds to about 5 minutes. For example, if the balloon is to be used to treat esophageal stenosis, a compliant balloon can be selected and inflated multiple times for about 5 seconds.

Other exemplary drug layer formulations are provided below in TABLE 2. It is understood that the combinations listed above or in TABLE 2 are not exclusive or limiting, and that any suitable drug(s) and excipient(s) for the desired indication can be used in the drug layer formulations.

TABLE 2

| Formulation | Drug (D) | Excipient(s) (E) | D:E Ratio |
| --- | --- | --- | --- |
| 1 | MF* | polysorbate | 1:1 |
| 2 | MF* | polysorbate | 1:1.3 |
| 3 | MF* | polysorbate | 1:2 |
| 4 | MF* | poly(ethylene glycol) | 1:1.3 |
| 5 | MF* | poly(ethylene glycol) | 1:2 |
| 6 | MF* | poly(ethylene glycol):polysorbate | 0.5:1:0.2 |
| 7 | MF* | poly(ethylene glycol):polysorbate | 1:1:0.05 |
| 8 | MF* | poly(ethylene glycol):polysorbate | 1:2:0.05 |
| 9 | MF* | poly(ethylene glycol):polysorbate | 1:1:0.2 |
| 10 | MF* | poly(ethylene glycol):polysorbate | 2:1:0.3 |
| 11 | MF* | poly(ethylene glycol):polysorbate | 2.5:1:0.3 |
| 12 | MF* | poly(ethylene glycol):polysorbate | 4:1:0.3 |
| 13 | MF* | poly(vinyl pyrrolidone):propylene glycol | 1:1:0.2 |
| 14 | MF* | poly(vinyl pyrrolidone):propylene glycol | 1:2:0.2 |
| 15 | MF* | poly(vinyl pyrrolidone):polysorbate | 1:1:0.03 |
| 16 | MF* | poly(vinyl pyrrolidone):polysorbate | 1:2:0.03 |
| 17 | MF* | poly(ethylene glycol):propylene glycol | 1:1:0:1 |
| 18 | MF* | poly(ethylene glycol):glycerol caproate | 1:1:01 |
| 19 | MF* | poly(ethylene glycol):glycerol caproate | 1:2:0.1 |

*Mometasone Furoate

Delivery Device

The expandable members described here can be delivered using any suitable delivery device. The delivery device can be configured to deliver the expandable member and can be used to move the expandable member into an expanded configuration. The expandable member can be loaded into the delivery device in the low-profile configuration, deployed from the delivery device at the treatment site, and then expanded (e.g., inflated, in instances when the expandable member is an inflatable structure) to the expanded configuration. Deploying the expandable member can comprise distally advancing the expandable member beyond the distal end of the delivery device. Alternatively, deploying the expandable member can comprise maintaining the expandable member at the desired location while proximally retracting the delivery device. Various ports, e.g., for irrigation and/or advancing viewing or imaging elements can also be included in the delivery device. Some variations of the delivery device can include features that protect against the loss of drug layered onto the expandable member upon advancement therefrom. Exemplary delivery devices can be found in co-pending U.S. patent application Ser. No. 16/436,363.

In some variations, the delivery device can comprise a short stiff catheter, for example, where a therapeutic treatment is being performed in the nasal passageways or sinus cavities where the distance from the point of insertion to the treatment site is relatively short. Other delivery devices can include a malleable tip, e.g., with a bending angle range of up to about 135 degrees, to aid in optimizing access to the frontal, sphenoid, or maxillary sinuses. In some other variations, the delivery device can comprise a small guiding catheter, an illuminated catheter, or an illuminated guidewire. For example, in variations in which the expandable member is delivered to the Eustachian tube, the delivery device can be configured to navigate to the cartilaginous part of the tube and can comprise a small guiding catheter that is sized and configured to avoid the bony part of the tube and the location of several critical arteries so as not to disrupt them. In further variations, the expandable member is delivered to the target tissue over a guidewire.

In some variations, the systems described here can comprise a sheath configured to cover the expandable member. The sheath can be used as an alternative to or in addition to a delivery catheter. The catheter and/or sheath can protect the drug layer from scraping off before or during delivery, keep the drug layer dry until deployment, and/or maintain the expandable member in the low-profile configuration. The sheath can be used with a non-compliant expandable member to return the device to a low-profile configuration, such that pleating or refolding of the non-compliant expandable member is not necessary post coating. Instead of a sheath, a topcoat could be layered onto the drug layer to protect it until deployment, as previously stated.

In some variations, the sheath can be elastic and can be expanded to be installed on and around the expandable member without moving or disrupting the drug layer, as described below. The sheath can be scored, perforated or otherwise configured to be removed from the expandable member once the expandable member is at the treatment site.

After the expandable member is inflated and the drug is transferred from the expandable member to the tissue, in some variations, the delivery device can also be used to remove the expandable member from the treatment site. In some variations, the inflation fluid can be removed from the expandable member in order to deflate the expandable member to a low-profile configuration. The delivery device can receive the deflated expandable member for removal by distally advancing the catheter over the expandable member, or proximally retracting the expandable member.

Methods

The expandable members described here can be delivered to target tissues of the nose, ear, or throat, and can be used for the treatment of conditions affecting those tissues. As previously described, in some variations, the expandable member can be delivered to a sinus cavity, sinus ostium, paranasal sinus, ethmoid sinus, inferior turbinate, middle turbinate, osteomeatal complex, and/or nasal cavity. The method can be for treating nasal conditions such as mucosal inflammation, including post-surgical inflammation, rhinosinusitis, and/or allergic rhinitis, and polypoid edema, for example. In other variations, the expandable member can be delivered to the Eustachian tube, external ear canal, and/or inner ear. The method can be for treating otic conditions such as post-surgical inflammation, otitis media, Meniere's disease, and/or tinnitus. In yet other variations, the expandable member can be delivered to the throat for the treatment of post-surgical pain, such as tonsillectomy pain, or for oncology (e.g., esophageal cancer), airway stenosis, chronic laryngitis, or epiglottitis. The expandable members can include a drug layer configured to locally deliver an active agent to the target tissue and provide sustained or extended release of the active agent at a therapeutic level for a desired period of time. In some variations, drug crystals or a combination of drug crystals and amorphous drug are included in the drug layer to provide a depot effect or adjust drug release kinetics.

The methods described herein can include locally delivering a therapeutically effective amount of an active agent to a target tissue by: 1) advancing an expandable member to a location within the ear, nose, or throat of the patient, the expandable member including a low-profile configuration and an expanded configuration, and a drug layer at least partially covering an outer surface of the expandable member, the drug layer including an active agent in the form of drug crystals; and 2) delivering the drug crystals to the target tissue by expanding the expandable member from the low-profile configuration to the expanded configuration so that the drug crystals contact the target tissue and form a depot in the target tissue that provides sustained release of the active agent for a period of time effective to treat a nasal, otic, or throat condition.

When the drug layer comprises less than about 60% of the active agent as drug crystals, the drug crystals can have an average length of less than about 80 μm. When the drug layer comprises at least about 60% of the active agent as drug crystals, the drug crystals can have an average length greater than about 80 μm. More specifically, when the drug layer comprises at least about 60% of the active agent as drug crystals, the drug crystals can have an average length greater than about 80 μm, greater than about 90 μm, greater than about 100 μm, greater than about 110 μm, greater than about 120 μm, or greater than about 130 μm. When the drug crystals have an average length of about 130 μm, it can be beneficial for the drug layer to comprise at least about 65% of the active agent as drug crystals. Other combinations of drug crystal amount in the drug layer and average drug crystal length can be used.

Furthermore, when the drug layer comprises drug crystals having an average length of less than about 80 μm, the drug layer can comprise less than about 60%, less than about 55%, less than about 50%, less than about 45%, less than about 40%, less than about 35%, less than about 30%, less than about 25%, or less than about 20% of the active agent as drug crystals.

In addition to containing drug crystals, the drug layer can also include the amorphous form of the active agent. Any active agent used to treat a nose, ear, or throat condition can be included in the drug layer, e.g., a corticosteroid can be employed. Mometasone furoate can be a useful corticosteroid to treat rhinosinusitis, polypoid edema, and tissue inflammation such as mucosal inflammation. The drug layer can further include excipients such as a poly(vinyl pyrrolidone), a polysorbate, a poly(ethylene glycol), propylene glycol, glycerol caprate, or combinations or mixtures thereof.

Some variations of the system and method include transferring substantially all the drug crystals from the expandable member to the target tissue with a single expansion. In other variations, the system and method includes using a single expandable member to treat multiple target tissue sites. For example, a single expandable member could be used to treat multiple sinuses (e.g., six different sinus ostia) in a patient. Here the drug layer can be formulated so that only a portion of the layer (and a portion of the drug crystals) is transferred with each expansion. The drug layer can also be configured, e.g., as multiple layers (sub-layers), to transfer one or more drugs over multiple expansions. Various surface treatments, e.g., plasma treatment or a hydrophilic primer layer, can also be applied to the expandable member to manipulate drug layer transfer rates. The expandable member can also be employed in systems and methods where it can beneficial to both dilate and deliver drugs to the target tissue.

Generally, the expandable members can be delivered in a minimally invasive fashion. In these instances, the expandable members can be delivered in a low-profile configuration. The expandable members can be preloaded in or on a delivery device, but need not be. Generally, at least a portion of the delivery device can be introduced into the body. In some variations, the delivery device can be introduced into a natural opening in the body, such as a nostril. In other variations, the delivery device can be introduced into an opening formed in the body via one or more procedures (e.g., a surgically-formed opening). In some of these variations, the artificially-created opening can be pre-formed using one or more tools that are separate from the delivery device. In some variations, one or more portions of the delivery device can be used to create the opening. In other variations, one or more portions of the expandable member can be used to create the opening.

Once the delivery device is introduced into the body, at least a portion of the delivery device can then be advanced to a target location. In some variations, this advancement can occur under direct visualization. The direct visualization can be achieved by a device external to the delivery device, such as an endoscope, or it can be achieved by one or more visualization devices separate from the delivery device, or it can be achieved by one or more visualization devices attached to the delivery device or disposed within one or more portions (i.e., a lumen of a cannula) of the delivery device. In some variations, electromagnetic localizer elements can be included on the expandable member or delivery device to enable navigation by an electromagnetic tracking technology. Additionally or alternatively, the advancement can occur under indirect visualization, such as fluoroscopy, ultrasound, or computer image guidance. In other variations, the delivery device can include an optical fiber that illuminates the position of the device with respect to the target tissue or area to be treated (e.g., a sinus). The illumination can be visible from outside the patient. In further variations, such as in some instances of delivery to the middle turbinate, the expandable member can be delivered without direct or indirect visualization.

After the expandable member is delivered to the target location, the expandable member can be expanded into an expanded configuration. In variations where the expandable member is expandable in response to one or more forces or stimuli, one or more appropriate forces of stimuli can be applied to the expandable member to expand the expandable member into an expanded configuration. For example, when the expandable member is an inflatable structure (e.g., a balloon), the inflatable structure can be expanded into an expanded configuration by delivery of a liquid or gas to the interior of the inflatable structure. In variations in which the expandable member is compliant, the expandable member can distend with inflation to the expanded configuration. In other variations, e.g., when the expandable member is pleated, folded, or wrapped to assume a low-profile configuration, upon inflation, the expandable member can unfurl to expand to the expanded configuration. In yet other variations, the expandable member can both distend with inflation and unfurl with inflation, for example, when the expandable member is semi-compliant. The expandable member in its expanded configuration can be shaped as shown in FIGS. 1A-1N. It is understood that other shapes can be employed that are tailored to the specific anatomy to be treated.

The expandable member can be expanded one or multiple times to transfer the drug layer, dilation of tissues, or both. Once expanded, the expandable member can be configured to conform at least partly to the shape of the bodily structure and substantially contact the bodily structure. For example, the expandable member can conform to the sinus or nasal cavity and substantially contact the sinus or nasal cavity wall. The percentage of surface area of the expandable member in contact with the cavity wall can be sufficient to transfer the drug layer and provide the appropriate delivery of one or more drugs to the tissue. For example, about 10% to about 100%, about 20% to about 100%, about 30% to about 100%, about 40% to about 100%, about 50% to about 100%, about 60% to about 100%, about 70% to about 100%, about 80% to about 100%, or about 90% to about 100% of the surface area of the expandable member can be in contact with the sinus or nasal cavity wall. In some instances, the expansion of the expandable member can act to anchor the expandable member against or into tissue. In other instances, it can be useful to control the direction of expansion to target a particular area for treatment. Directional expansion can be achieved using a directional balloon (e.g., as shown in FIGS. 1F and 1L), or by including as part of the delivery system, a rotatable sheath with an opening or cut-out that is capable of exposing only the intended surface area of the expandable member for targeted expansion and tissue contact, or for directionally anchoring the expandable member against the tissue for increased contact.

As mentioned above, the pressure of the expandable member when expanded can be sufficient for maintaining contact of the surface against the sinus or nasal mucosa, or other bodily structure described herein, but not cause unwanted damage or reshaping. For example, when the expandable member is a compliant balloon, the inflation pressure of the compliant balloon can be between about 2 atm and 16 atm, more specifically between about 4 atm and 6 atm.

The expandable member can be left in place for any suitable amount of time. It can be desirable for the expandable member to be left in place for a sufficient period to transfer the drug layer and deliver one or more drugs to the tissue. As previously described, the drug layer can be formulated with a high drug-to-excipient ratio to enhance fast release from the expandable member during a short time period of inflation. Expansion times (e.g., inflation times) ranging from under one minute to a few hours can be utilized for ear and nasal applications for enhanced drug uptake. For example, in some variations the expandable member can be left in place (expanded) for about 5 seconds to about 2 hours, about 30 seconds to about 2 hours, about 5 minutes to about 1 hour, about 30 seconds to 5 minutes, about 5 seconds to about 5 minutes, or about 10 minutes to about 30 minutes. In some variations, the expandable member and/or drug layer is structured so that a physician can control the amount of coating (and thus, drug) delivered by controlling the expansion time (e.g., inflation time). In other words, the amount of drug delivered can be based on the duration of expansion at the one or multiple tissue sites, e.g., one or more paranasal sinuses. In another variation, the expandable member is left in place for about 5 seconds. In a further variation, immediate transfer of the drug is accomplished with a duration of expansion of less than 5 seconds. A shorter expansion time can result in overall less mucosal injury and thus can be beneficial when drug delivery to multiple sinuses or target sites is to be performed. In some variations, the entire procedure can be performed during a single doctor office visit. In other variations, where the expandable member is to be left expanded and in place for longer periods of time (e.g., 1-2 hours), the expandable member can comprise a pressure valve that the patient can release him/herself outside of the doctor's office.

In further variations, multiple expansion-collapse cycles (e.g., inflation-deflation cycles) of the same expandable member could be used to release multiple coating layers to a single or multiple tissue sites. Each inflation-deflation cycle could be of the same or different duration. In some instances, a single expandable member can be repeatedly expanded to treat multiple/different sinuses. For example, a single expandable member can be used to treat two to eight sinuses. Specifically a single expandable member such as a balloon can be expanded and used to deliver its drug layer to two sinuses, three sinuses, four sinuses, five sinuses, six sinuses, seven sinuses, or eight sinuses, for a total of two balloon inflations, three balloon inflations, four balloon inflations, five balloon inflations, six balloon inflations, seven balloon inflations, or eight balloon inflations, respectively. In one variation, a single expandable member can be used to treat two frontal sinuses and two maxillary sinuses and/or two sphenoid sinuses. In other variations, multiple expansions can be used to transfer drug across inferior and middle turbinates.

Upon transference of the drug layer from the expandable member to the tissue, the delivery device and expandable member can be removed. Prior to removal, the expandable member can be collapsed or otherwise returned to a low-profile configuration. As described above, in variations in which the expandable member comprises an inflatable device, the inflation fluid can be withdrawn from the expandable member and the expandable member deflated to the low-profile configuration. When multiple inflations are to be performed, the inflatable device can be configured to rapidly deflate or collapse back to its pleated/folded state to prevent loss of the remaining drug. The delivery device can then be used to receive the expandable member and the expandable member and delivery device removed from the body, or the expandable member can be removed without the use of the delivery device, or using a separate device.

After the drug layer is transferred to the tissue, the active agent can be eluted gradually over time. For example, the drug layer can include drug crystals that provide sustained release of the active agent at a therapeutic level for a period of days, weeks, or months. In some variations, a therapeutic level of drug delivery can be provided for up to 5 days, up to 14 days, up to 30 days, up to 45 days, up to 60 days, up to 75 days, or up to 90 days, depending on the specific treatment application. In other variations, the treatment time can range from about 2 months to about 3 months. For example, when the method is intended for treatment of allergic rhinitis applications, it can be desirable to maintain a therapeutic level of drug for the duration of an allergy season (e.g., about 2 months to about 3 months). When a drug is to be delivered after functional endoscopic sinus surgery (FESS), the formulation can be configured to release the drug over a period of about 14 to 28 days. When a drug is to be delivered after balloon sinuplasty alone, the formulation can be configured to release the drug over a period of about 7 to 14 days.

In some instances, the method of treatment can comprise multiple rounds of treatment. For example, patients who suffer from chronic conditions, such as otitis media, or who experience more than one allergy season (e.g., due to different allergens) each year, can get multiple treatments during the year. This can provide continuous therapeutic treatment in healing the condition and/or sustained relief from the symptoms associated with the condition.

For applications where long-term mechanical support is desirable, the methods described herein can be combined with an implantable device. For example, the methods described herein can be combined with the placement of a scaffold or stent. In some variations, the scaffold or stent can be drug eluting. In some variations the scaffold or stent can be expandable (e.g., balloon expandable or self-expanding). In some variations, the scaffold or stent can be bioresorbable (e.g., comprise a bioresorbable synthetic biopolymer), but need not be.

When the methods described herein are combined with an implantable device, the expandable members described herein can be used to deliver a drug before implantation of the implant, or can be used post-implantation of the implant. In variations in which the expandable member is used first, the device can help pre-dilate the ostia for improved ease of delivery and implantation of the implant. In variations in which the expandable member is used second, the device can help post-dilate the implant for improved apposition. In addition to helping deliver an effective localized dose of a drug, when combined with a scaffold or stent, the methods described here can, for example, maintain the patency of the sinus cavities, and help prevent obstruction caused by adhesions between healing or inflamed mucosal surfaces.

Figure 6:
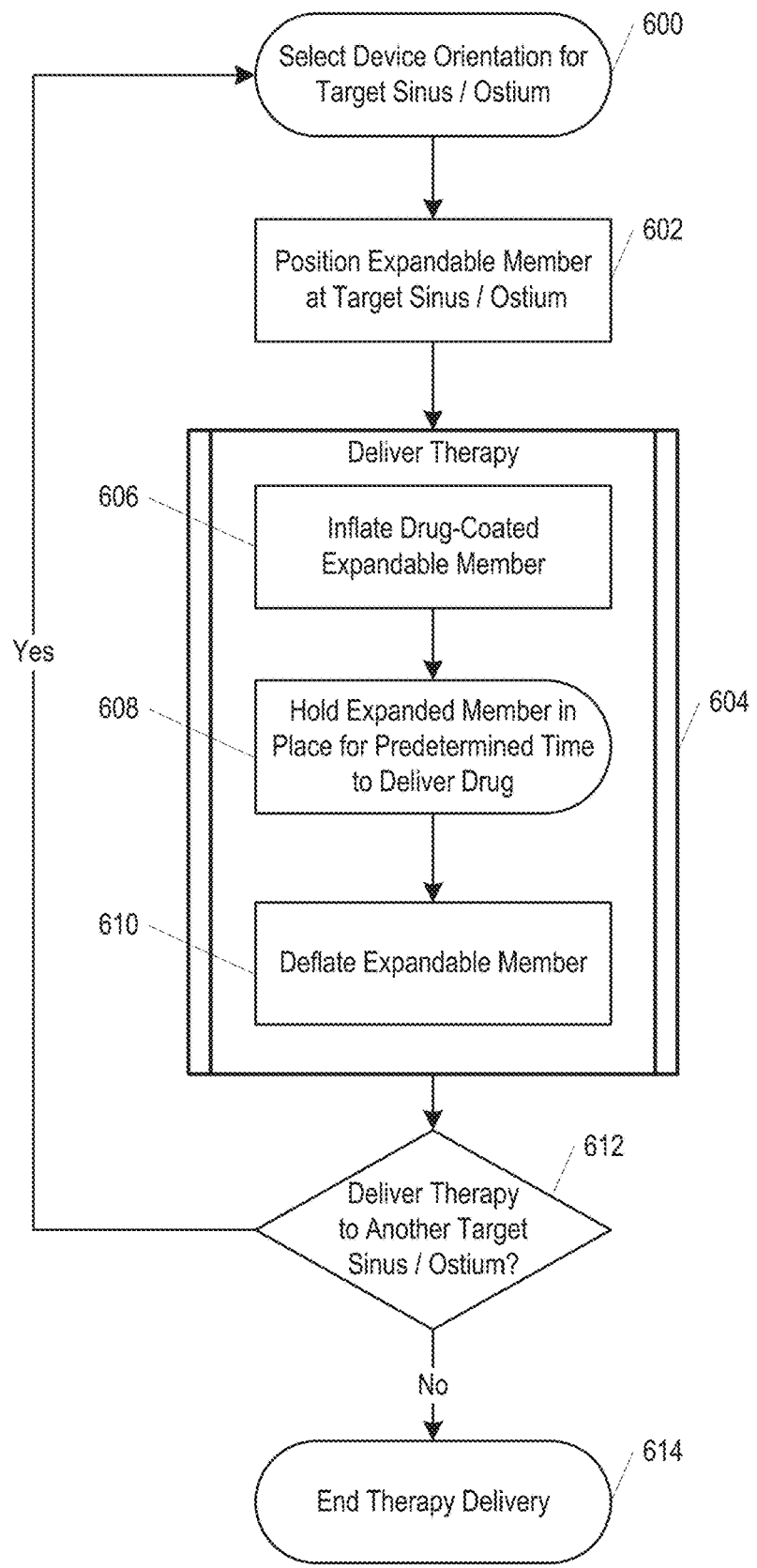
FIG. 6 is a flowchart that illustrates an exemplary process delivering therapy with a drug-coated expandable member.

In some variations, the methods include the process described in FIG. 6. FIG. 6 is a flowchart that illustrates an exemplary process delivering therapy to a patient with a drug-coated expandable member. At step (600), a delivery device for the expandable member is configured into an orientation such that the expandable member will be delivered to a target sinus or ostium. At step (602), the expandable member is positioned at the target sinus or ostium with the delivery device. At step (604), a repeatable step, therapy is delivered to the target sinus or ostium. The therapy delivery includes the following steps: at step (606), the drug-coated expandable member is inflated such that the external surface of the expandable member is in contact with the target tissue; at step (608), the expanded expandable member is held in place for a predetermined period of time, thereby transferring drug from the expandable member to the contacted tissue; and at step (610), the expandable member is deflated. The therapy delivery of step (604) can be performed one or more times at any given target sinus or ostium. At decision step (612), a determination is made whether or not a therapy needs to be delivered to a further target sinus or ostium—if "Yes", then the process returns to step (600); if "No", then the process proceeds to step (614), completely withdrawing the expandable member from the patient and ending the delivery of therapy.

Manufacturing

The devices described herein can be made in any suitable manner. In general, molds can be used to form expandable members designed for specific anatomies, and the materials selected for the expandable member can be based on desired compliance for the specific application.

Figure 2:
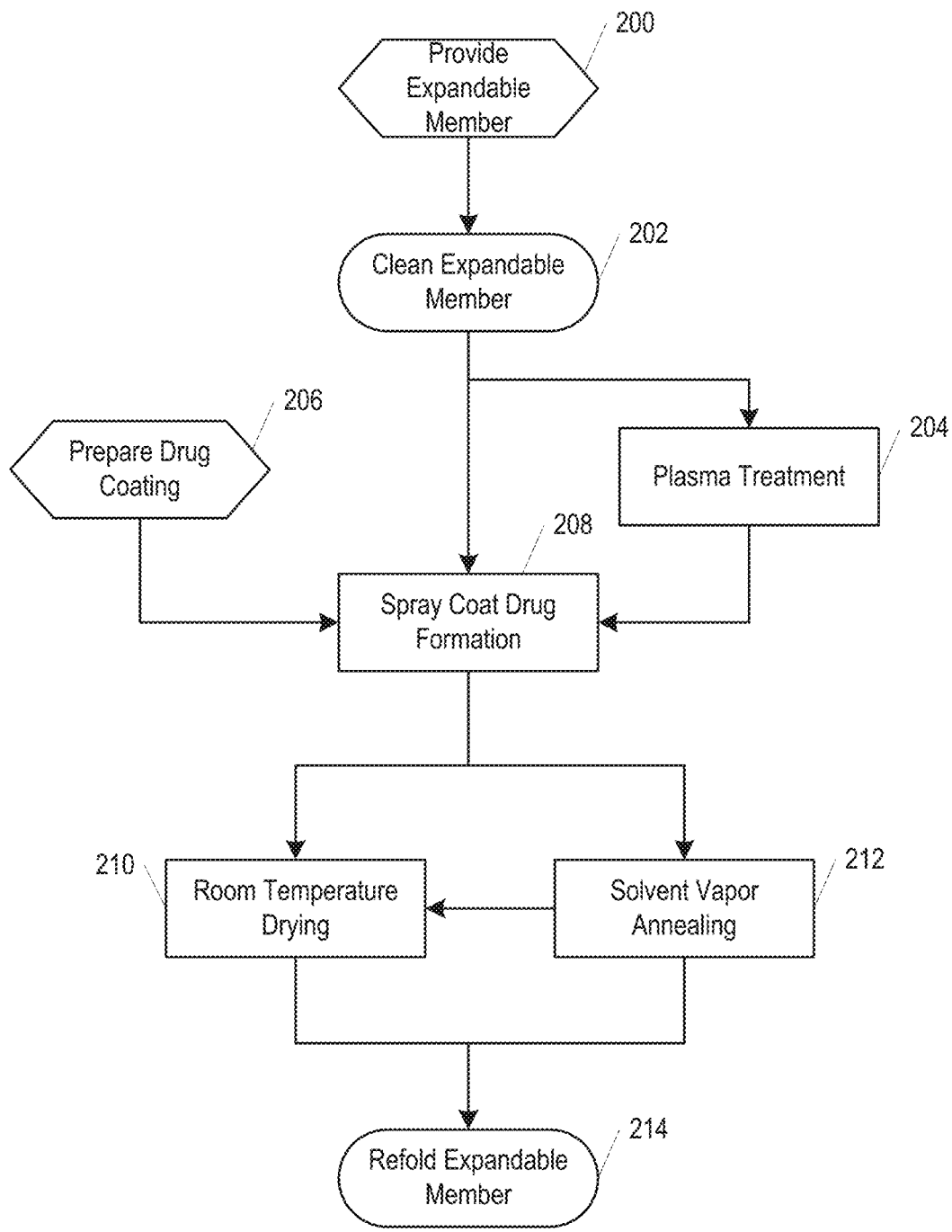
FIG. 2 is a flowchart that illustrates exemplary processes for coating the expandable member.
Figure 3:
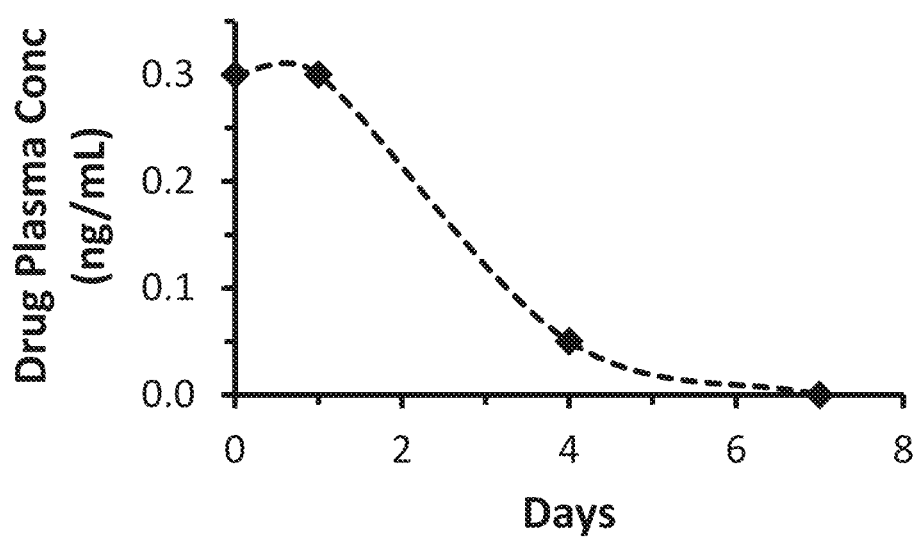
FIG. 3 is a graph that illustrates the blood plasma concentration of mometasone furoate after delivery of a drug layer to an ovine maxillary sinus over a seven (7) day period.

FIG. 2 is a flowchart that illustrates exemplary processes for coating the expandable member. At preparation step (200), an expandable member, (e.g. a balloon) can be provided in a folded, collapsed, partially inflated, fully inflated, or partially deflated configuration. At step (202), the expandable member is cleaned prior to having any active pharmaceutical ingredient being applied to the surface of the expandable member. Optionally, at step (204), the expandable member can be further subjected to a plasma treatment process which can further clean the surface of the expandable member. At step (206), a drug coating is prepared to be sprayed on to the expandable member. At step (208), the cleaned expandable member is sprayed with the prepared drug coating. Following spraying the expandable member with a drug coating, the expandable member can be dried at room temperature as shown at step (210). Alternatively, following spraying the expandable member with a drug coating can be subjected to a solvent vapor annealing process as shown at step (212). Optionally, the expandable member with a drug coating can additionally be dried at room temperature after solvent vapor annealing. At step (214), following either or both of room temperature drying and solvent vapor annealing, the expandable member is crimped (or re-folded). The process set forth above is described in further detail below.

Active agents can be layered (e.g., coated) on the expandable member when fully inflated, partially inflated, or folded. Coating an expandable member such as a balloon while inflated and then deflating the balloon so that delivery to the target tissue site occurs its collapsed state can maximize drug delivery and tissue coverage. In variations where the expandable member is folded, the drugs can be layered on the regions of the expandable member that become protected upon folding of the expandable member. This can help to protect the drug layer during delivery or loading into a delivery device or sheath. Pleat geometry such as pleat number, length, and shape can be adjusted for the desired amount of drug coverage during refold. For example, an elongate cylindrical balloon having a diameter of six millimeters (6 mm) and six (6) pleats can be useful in minimizing drug loss during balloon delivery and refolding. In contrast with four (4) pleats used with 6 mm diameter balloons, employing more pleats such as five (5) or six (6) pleats can be beneficial for refolding to the collapsed state and thus help keep the drug layer on the balloon (and minimize drug loss) in between multiple expansions of the balloon. Tight refolding to a low profile can be beneficial in keeping drug loss during delivery but prior to inflation at less than about 10%. In further aspects, tight refolding to a low profile can be beneficial in keeping drug loss during delivery but prior to inflation at less than about 5% of drug load. This selective layering can be achieved by masking of the region that is desired to be non-layered. In other variations, drugs can be layered on a portion of the expandable member based on a desired treatment area within the target cavity. For example, an expandable member intended for use in the nasal cavity can be coated or layered on one side to deliver drug to the turbinates, but uncoated on a second side to minimize drug delivery to the nasal septa (e.g., to prevent any deterioration of the septa). An expandable member to be used at multiple treatment sites and/or expanded multiple times can be provided with multiple layers of drug.

In some implementations, the plasma treatment can be under vacuum, using gases such as oxygen ($O_2$), inert gases such as argon (Ar), or combinations thereof. Controlled parameters for the plasma treatment process can include the number of cycles of plasma treatment, the cycle duration and total duration of the plasma treatment, the power at which the plasma arc is operated, and the flow of the one or more gases used for the plasma treatment. For example, the plasma treatment process can have one or more cycles of exposing the surface of the expandable member to plasma. In some aspects, each cycle of the plasma treatment can last from about three minutes to about fifteen minutes, or for a period of time within that range. In other aspects, the power of the plasma arc can be operated in a range of from about forty to about four hundred Watts (40-400 W), or at increments or gradients of power within that range (such as 50 W, 100 W, 150 W, 200 W, 250 W, 300 W, or 350 W). In various aspects, the power source of the plasma arc torch can be AC, DC, or RF. In further aspects, the gas flow of the one or more gasses can each be at a rate of about five to about fifty cubic centimeters per minute (5-50 cc/min), or at increments or gradients of gas flow within that range (such as 10 cc/min, 15 cc/min, 20 cc/min, 25 cc/min, 30 cc/min, 35 cc/min, 40 cc/min, or 45 cc/min). In configurations where two or more gases are flowed as part of the plasma treatment, the gases can be uses concurrently, alternatingly, or sequentially, and the two or more gases can be operated at the same flow rate or at different flow rates. In other implementations, the plasma treatment can be a real-time or "just-in-time" process using atmospheric plasma, allowing for a continuous treatment of expandable devices fed through the plasma conditioning.

In some variations, the drug layer can be patterned on the expandable member or provided on specific areas of the expandable member, depending on, e.g., the anatomy or particular target tissue site to be treated. For example, the pattern could include solid or dashed lines of the drug layer, the drug layer dotted on the expandable member, or the drug layer provided as a spiral around the expandable member, etc. The thickness of the drug layer can range from about 10 µm to about 500 µm. In some variations, the thickness of the drug layer can be varied, e.g., structured to be thicker on some areas of the expandable member than others.

The drug layer can be formed on the expandable member by methods such as spray coating, pipette or syringe coating, or dip coating. Spray coating can achieve improved tissue uptake and drug delivery uniformity. Spray coating can provide homogenous distribution of the drug in the coating. In some implementations of spray coating, the drug or other active pharmaceutical ingredient ("API") can be dissolved within an appropriate solvent such that the drug or other API can be applied as a liquid or gas through a spray coating system. In some embodiments, the spray coating system can be an air atomizing system, a heated fluid/gas flow system, an ultrasonic system, a pressurized or compressed air system, hydraulically-actuated systems, electrically-actuated systems, manifold or individual nozzle systems, or combinations thereof. The flow rate of drug or other API through a spray coating system can range from about 0.005 ml/min to about 1.000 mL/min, or at increments of volume per time within that range. The spray coating system can be set up that the expandable member is adequately coated with the spray while being held in a static configuration. Alternatively, spray coating system can be set up that the expandable member is adequately coated with the spray while being rotated and/or otherwise translated or manipulated to expose the complete external surface area to the spray coating.

The total amount of drug in the drug layer formed on the expandable member by these manufacturing techniques can be from about 0.1 mg (100 µg) to about 20 mg (20,000 µg), or even up to 45 mg (45,000 µg). The density of drug in the drug layer distributed across the expandable member by these manufacturing techniques can be from between about 1 µg/mm² to about 11 µg/mm².

For improved drug layer adhesion, the expandable member can be cleaned with a solvent and dried prior to coating. In addition, plasma treatment with an inert gas, such as argon or oxygen, after cleaning can increase the cleaning and wettability of the expandable member surface leading to increased coating adhesion and release of the coating upon contact with mucus at the mucosal tissue site. One or more parameters of the plasma treatment can be altered to adjust drug release to the desired rate. For example, power, flow rate of the inert gas, cycle time, and number of cycles can be manipulated to adjust the rate of drug release. In some variations, the expandable member can be primed with a hydrophilic excipient to enhance drug release. In other variations, the expandable member can be primed with a hydrophobic (lipophilic) excipient to slow drug release. The hydrophilic to lipophilic properties of the excipient are selected for either a faster or slower release rate. The priming can be performed alone or in addition to cleaning and plasma treatment.

After coating of the expandable member, e.g., a balloon, the expandable member can be re-folded at an elevated temperature, e.g., at about 50 degrees Celsius, about 60 degrees Celsius, about 70 degrees Celsius, or about 80 degrees Celsius, and for about 5 minutes, about 30 minutes, or about one hour, to achieve a low profile. In some variations, the balloon can be re-folded (or crimped) under vacuum at a reduced pressure and temperature while applying vacuum to its interior volume to obtain a low profile. Re-folding of the expandable member can be followed by sheathing, packaging in a foil pouch with argon, nitrogen or other inert gas, and sterilization using gamma irradiation or electron beams.

In some variations, the manufacturing method can include cleaning the balloon surface and/or treating the balloon with plasma, inflating the balloon, spray coating the balloon with a drug layer formulation, drying the balloon coating at room temperature or elevated temperature, and re-folding the balloon as described above.

In other variations, the manufacturing method can include cleaning the balloon surface and/or treating the balloon with plasma, inflating the balloon, spray coating the balloon with a drug layer formulation, exposing the coated balloon to a solvent vapor (solvent vapor annealing), and re-folding the balloon as described above. These manufacturing processes are outlined in FIG. 2. Suitable solvent vapors can include, but are not limited to, water, acetone, methanol, ethanol, 2-propanol, 1-propanol, linear alcohols, methane, ethane, propane, butane, pentane hexane, cyclohexane, heptane, methyl iso-butyl ketone, methyl ethyl ketone, dimethylsulfoxide, dimethylacetamide, dimethylformamide, formamide, methyl acetate, ethyl acetate, propyl acetate, isopropyl acetate, n-butyl acetate, dimethyl ether, diethyl ether, dipropyl ether, N-methylpyrrolidone, dichloromethane, chloroform, difluoromethane, fluoroform, freons, benzene, toluene, xylene, blends thereof, and combinations thereof. The preferred vapor can depend on a number of variables such as the compositions of the drug layers and surfaces of the expandable device. In further variations, the manufacturing method includes drying the balloon drug layer at room temperature and exposing the layered balloon to a solvent vapor.

In addition to initial drug concentration in solution and drug density of the drug layer, the manner in which the drug layer is dried, mode of sterilization, and/or exposure to solvent vapor can affect the amount of crystallization in the drug layer. Thus, one or more of these parameters can be manipulated during manufacturing to vary the amount of the crystalline form of the drug in the drug layer. For example, the particular solvent vapor used, solvent vapor annealing temperature, duration of solvent vapor exposure, solvent vapor pressure, and/or evaporation rate (e.g., slower drying) during drug layering and post-layering can be used to control the crystallinity of the drug. In some variations, acetone vapor can be used for the SVA process to promote drug crystallinity. Further variations can include a mixture of acetone and isopropyl alcohol (IPA), ranging from a 90:10 ratio of acetone:IPA to a 50:50 ratio of acetone:IPA. Exposure to electron beams can also be used to initiate drug crystallization. In variations where shorter periods of drug delivery are needed, faster drying, shorter exposure to solvent vapor, or a particular solvent vapor can be used to provide more amorphous drug in the coating. Thus, in some instances the manufacturing methods can be tailored to provide a drug layer that includes a crystalline form of the drug. In other instances, the manufacturing methods can be tailored to provide a drug layer that includes the amorphous form of a drug. In yet further instances, the manufacturing methods can be tailored to provide a drug layer having a mixture of crystalline and amorphous forms of a drug.

In some implementations, the SVA process can be run at an operational temperature of about 30.0° C.±0.5° C. to about 50.0° C.±0.5° C., or at increments or gradients of temperature within that range (e.g., 31.0° C., 32.5° C., 33.3° C., 35.0° C., 36.9° C., 38.8° C., 40.0° C., 45.0° C., 48.4° C., etc.). Of course, a particular solvent may have an operational temperature for SVA less than 30.0° C. or greater than 50.0° C. In some implementations, the duration of the exposure to the solvent vapor can be from about fifteen minutes (15 min.) to about two hundred forty minutes (240 min.), or increments or gradients of time within that range (e.g., 30 min., 45 min., 60 min., 90 min., 120 min., 150 min., 180 min., etc.). The volume of a solvent used in the SVA process will be dependent at least on the size of the expandable member to treat and the determined duration of the SVA process. In some implementations, the duration of drying or settling of the vapor on the surface of the expandable device can be from about fifteen minutes (15 min.) to about two hundred forty minutes (240 min.), or increments or gradients of time within that range (e.g., 30 min., 45 min., 60 min., 90 min., 120 min., 150 min., 180 min., etc.).

For example, the manufacturing methods can be manipulated to provide a drug layer including about 100% amorphous drug, about 5% to about 10% of crystalline drug (and about 90% to about 95% amorphous drug), about 20% to about 25% crystalline drug (and about 75% to about 80% amorphous drug), about 50% crystalline drug (and about 50% amorphous drug), about 60% crystalline drug (and about 40% amorphous drug), about 70% crystalline drug (and about 30% amorphous drug), or about 75% crystalline drug (or about 25% amorphous drug). In one variation, the drug layer comprises at least about 60% of the active agent as drug crystals. In another variation, the drug layer comprises less than about 60% of the active agent as drug crystals. For the treatment of nasal or mucosal conditions, it can be useful for the drug layer to provide mometasone furoate in crystalline or amorphous forms, or a combination of crystalline and amorphous forms. In some variations, about 25% to about 75% of the mometasone furoate is provided in crystalline form in the drug layer.

In a specific example, an SVA process using acetone within the parameters identified above applied on a batch of twenty (20) expandable balloons produced drug layers having 58.9%±3.7% crystalline drug, where the major axis of the crystals formed had an average length of 103.8 µm±8.7 µm and where the minor axis of the crystals formed had an average length of 59.5 µm±5.5 µm. More broadly, crystals formed on expandable devices according to the processes described herein can be expected cover at least 50% of the surface area of the target device, to have a major axis length of from 95 µm to 120 µm, and a minor axis length of from 50 µm to 70 µm.

It can be appreciated that allowing a stabilization time for crystal formation after the actual SVA process (and before refolding the expandable member) can further promote crystal growth and coverage on an expandable device. In other words, the crystals formed on an expandable device can, immediately following SVA, can continue to grow and/or interconnect such that the percentage of drug layer surface area that is in crystalline form increases and such that the average major and minor lengths of the crystals also increases.

Other manufacturing conditions for the expandable member (e.g., a balloon) such as roughening the surface of the expandable member and use of crystallization initiators can also affect the amount of the outer surface of the expandable member covered by the crystalline drug layer, crystal size, and crystal geometry. Roughening the surface of the expandable member can be accomplished by such processes as sandblasting, forming the expandable member with a roughened mold, or by chemical treatment. In other variations, drug crystallization can be enhanced by creating imperfections (e.g., microcracks, delamination) in the drug layer. When the expandable member is a balloon, this can be achieved by deflating and inflating the balloon after the drug layer process. Seeding of the balloon surface with a primary coating of drug or excipient crystals can also facilitate crystallization.

In addition to mechanical delivery from a high pressure member such as a balloon, the use of drug crystals in a balloon coating can extend the release and in vivo exposure of the drug beyond the rapid release from the balloon when it is initially expanded. In some variations, the inflation pressure used to expand the drug-coated balloon is used to adjust drug delivery. Here the inflation pressure can range from about 2 atm to about 12 atm or from about 10 atm to about 12 atm. In other variations, drug delivery can be adjusted so that it is a function of balloon outer diameter. The balloon inflation pressure and/or outer diameter can be used to embed drug crystals into the nasal mucosa by mechanical force from the balloon dilation. In turn, the balloon dilation can create microtears in the nasal mucosa that enable deposition of drug crystals into the mucosa, which are retained in the tissue after deflation of the balloon.

In addition to the particular components of the drug layer formulation, the manufacturing methods described herein can help minimize drug loss during delivery to the treatment site and maximize drug delivery upon inflation and contact with tissue.

EXAMPLES

The following examples are illustrative only and should not be construed as limiting the disclosure in any way.

Example 1

Manufacture of an Expandable Device Layered with Drug Crystals

Expandable members were made by spray coating 6 mm×20 mm semi-compliant balloons with a drug layer formulation. The drug layer formulation included either a 1500 µg or 3000 µg dose of mometasone furoate, poly (ethylene glycol), and a polysorbate. The drug layered balloons were then exposed in an acetone solvent vapor for 30 minutes. The resulting drug crystallization characteristics (average balloon crystal coverage (percent of the active agent as crystals in the drug layer) and average crystal length) under these manufacturing conditions is provided below in TABLE 3.

TABLE 3

| Dose (µg) | Average % Drug Crystals | Average Crystal Length (µm) |
|---|---|---|
| 1500 | 36.4 | 78.7 |
| 3000 | 64.9 | 124.0 |

Example 2

Tissue Concentration of Mometasone Furoate After Balloon Expansion in Eustachian Tubes The Eustachian tubes of eight domestic sheep were accessed transnasally using balloon catheters having drug layers containing 1500 µg of mometasone furoate. The balloon catheters were made as described in Example 1. A singe balloon catheter was expanded to 12 atm of pressure to deliver the mometasone furoate crystals to Eustachian tube tissue and to dilate each contralateral Eustachian tube at its proximal opening. The animals were sacrificed at either 7 days or 30 days after balloon expansion, and mucosa from each Eustachian tube collected and frozen. Mometasone furoate concentration was then quantified using liquid chromatography mass spectrometry (LCMS). The maximum mometasone furoate tissue concentrations were found to be 47 µg/g at 7 days, and 0.2 µg/gm at 30 days, demonstrating that therapeutic tissue levels (i.e., at least 0.1 µg/gm) of mometasone furoate can be maintained for a 30 day treatment period.

Example 3

Tissue Concentration of Mometasone Furoate After Two Balloon Expansions in Sinus Ostia Therapeutic levels of mometasone furoate can be achieved at the target tissue site after two expansions of a drug layered balloon. In this Example, drug layered balloons were made according to Example 1 and used to dilate sheep frontal ostia. As shown below in TABLE 4, two expansions of the 3000 µg dose balloons resulted in an average percent mometasone furoate (MF) release per inflation of 30% (Study Arm 1). When placed in bloody sheep frontal sinus ostia (Study Arm 2), the resulting average percent MF release per inflation was 28%, showing that the in vivo release rate from the balloon is not impacted by blood present in the sinus. Average tissue MF concentrations (8 sinus ostia studied per time point) were then obtained as a result of the expansions performed for TABLE 4, and are presented in TABLE 5 for both study arms. The average tissue MF concentrations for the frontal sinus ostia were at or above therapeutic levels at all time points.

TABLE 4

| MF Dose | Study Arm | # of Devices (n) | Average MF Release per Inflation (µg) | Average % MF Release per Inflation |
|---|---|---|---|---|
| 3000 µg | 1 | 32 | 889 | 30 |
|  | 2 | 4 | 854 | 28 |

TABLE 5

| MF Dose | Study Arm | Time Point (days) | Average Tissue MF Concentrations (µg/g) | |
|---|---|---|---|---|
| | | | Frontal Sinus Ostia | Nasal Passage |
| 3000 µg | 1, 2 | Approx. 1 hour after inflation | 141.92 | 4.73 |
| | | 7 | 9.89 | 0.06 |
| | | 14 | 1.25 | 0.02 |
| | | 30 | 0.10 | 1.38 |

When balloons including a mometasone furoate dose of 1500 µg were expanded in the sheep frontal sinus ostia, the average percent MF release per inflation was similar to the 3000 µg dose balloon over two expansions. As shown below in TABLE 6, the average percent MF release per inflation was about 23%. Average sheep frontal sinus MF concentrations for four sinuses and plasma obtained at 30 days post the two expansions are presented in TABLE 7 for both study arms. The average tissue MF concentrations for the frontal sinus ostia studied was above the therapeutic level of 0.1 µg/gm at 30 days, while plasma levels were below the limit of quantitation, showing that drug delivery remains local within the sinuses during the treatment period.

TABLE 6

| MF Dose | Number of Inflations | Study Arm | Number of Devices (n) | Average MF Release per Inflation (µg) | MF Release (% MF Dose) |
|---|---|---|---|---|---|
| 1500 µg | $1^{st}$ | 2 (treatment) | 4 | 524 | 35 |
| | $2^{nd}$ | 1 (treatment) | 4 | 176 | 12 |
| | Average over first two inflations | NA | NA | 350 | 23 |

TABLE 7

| MF Dose | Explant Timepoint (days) | MF Concentration Frontal Sinus Ostia Tissue (µg/g) | MF Concentration Plasma$^a$ (pg/mL) | Total MF Released (µg) |
|---|---|---|---|---|
| 1500 µg | 30 | 5.00 | BLQ | 350 |

$^a$BLQ = Below Limit of Quantitation (≤20.0 pg/mL); analytical range is 20.0-1000.0 pg/mL.

Example 4

Clinical Effect of Therapy on Inflammation and Polypoid Edema

A prospective, multicenter, randomized, blinded clinical trial was run in a population of patients (N=70, age≥18 years old) who previously had FESS and who had polypoid edema in their frontal sinuses. Each patient had one of their two frontal sinuses dilated (treated) with a drug-coated balloon including mometasone furoate (a 3000 µg dose), poly(ethylene glycol), and a polysorbate. Conveniently, the other sinus of each patient was dilated with a non-drug-coated balloon (otherwise using the same balloon, structurally) for use as an intra-patient control.

TABLE 8

| | Treatment Side (N = 70) | Control Side (N = 70) | Mean Diff./ Relative Diff. | p-Value |
|---|---|---|---|---|
| Independent Reviewer at Day 14 | | | | |
| Polypoid edema grade, mean (SD) | 1.5 (0.91) | 1.7 (1.00) | −0.3 (0.97) | 0.0412 |
| Independent Reviewer at Day 30 | | | | |
| Inflammation score, mean (SD) | 39.7 (28.20) | 47.3 (31.47) | −7.7 (25.32) | 0.0185 |
| Polypoid edema grade, mean (SD) | 1.3 (0.95) | 1.6 (0.96) | −0.3 (0.94) | 0.0257 |

TABLE 8-continued

|  | Treatment Side (N = 70) | Control Side (N = 70) | Mean Diff./ Relative Diff. | p-Value |
| --- | --- | --- | --- | --- |
| Need for oral steroid interventions, N (%) Clinical Investigators Day 30 | 18 (28.6) | 27 (42.9) | −33.3 | 0.0490 |
| Inflammation score, mean (SD) | 31.9 (32.54) | 45.8 (35.23) | −13.9 (39.71) | 0.0057 |
| Polypoid edema grade, mean (SD) | 0.9 (0.89) | 1.3 (0.97) | −0.4 (1.03) | 0.0057 |

In particular, three metrics that were measured and/or tracked over time as shown in TABLE 8 to judge the effect of the drug coated balloon on patients showed both clinical and statistical significance. First, the polypoid edema grade within the patients was measured at Day 14 by an independent reviewer, and then the polypoid edema grade was further measured at Day 30 by both the independent reviewer and by the respective clinical investigators. Second, the inflammation score was measured at Day 30 by both the independent reviewer and by clinical investigators. Finally, the need for oral steroid intervention was determined at Day 30 by the independent reviewer.

Differences in measurements performed by the independent reviewer as compared to the various clinical investigators can be attributed to the difference in their respective evaluation positions. Generally, an independent reviewer is thought to have a more objective and blinded perspective when evaluating clinical results, however, the independent reviewer in this study was limited to a post-procedure video review (only a two-dimensional evaluation). In contrast, the clinical investigators, while remaining blinded to which of the balloons had a drug coating, were able to evaluate the results with real-time video combined with tactile probing and response with instruments (a three-dimensional evaluation). Additionally, the clinical investigators also have familiarity with their respective patients who participated in the clinical study, giving the clinical investigators an impression of individual improvement over time.

The polypoid edema grade in the frontal recess/frontal sinus ostium was based on a 4-point scale, as follows: "0" indicating a normal mucosa, no visible polyps/mucosal edema; "1" indicating a minimal amount of polyps/mucosal edema; "2" indicating a moderate amount of polyps/polypoid edema; and "3" indicating an expanded amount of polyps/polypoid edema. Accordingly, on this 4-point scale, a relative difference of 0.4 point would represent approximately a 10% difference in polypoid edema burden.

The results as shown in TABLE 8 indicate that treatment with a drug-coated balloon leads to a substantive improvement of polypoid edemas, summarized as follows. The polypoid edema scores of the treated sinuses were about 0.3 lower as compared to the control sinuses at Day 14 as measured by the independent reviewer, leading to a 14.5% relative reduction in polypoid edema burden. The polypoid edema scores of the treated sinuses were about 0.3 lower as compared to the control sinuses at Day 30 as measured by the independent reviewer, leading to a 16.7% relative reduction in polypoid edema burden. Further, the polypoid edema scores of the treated sinuses were about 0.4 lower as compared to the control sinuses at Day 30 as measured by the clinical investigators, leading to a 27.9% relative reduction in polypoid edema burden.

The inflammation score was based on a 100-point scale, where a relative difference of 10 points would represent a 10% difference in inflammation severity.

The results as shown in TABLE 8 indicate that treatment with a drug-coated balloon leads to a substantive improvement of tissue inflammation at the target tissue exhibiting polypoid edema, summarized as follows. The inflammation scores of the treated sinuses were about 7.7 lower as compared to the control sinuses at Day 30 as measured by the independent reviewer, leading to a 16.2% relative reduction in inflammation. The inflammation score of the treated sinuses were about 13.9 lower as compared to the control sinuses at Day 30 as measured by the clinical investigators, leading to a 30.2% relative reduction in inflammation.

Often in nasal polyp removal procedures, a patient is given an oral steroid subsequent to the procedure. Oral steroids are generally systemic in effect, not local, and can have undesirable side effects affecting other parts of the body then than the target tissue to be treated. Accordingly, a reduction in the need for oral steroid treatment, here in the post-sinus surgery context, can be considered a meaningful benefit to patients.

The results as shown in TABLE 8 indicate that treatment with a drug-coated balloon leads to a substantive reduction in the need for oral steroid intervention (prescription) in patients. Specifically, the need for oral steroid intervention was reduced by about 33% as evaluated at Day 30 by the independent reviewer.

It is reasonable to expect that the results of the clinical trial described in Example 4 can be improved upon with further refinement of the drug-coated balloon manufacturing process, upgrades to the drug-coated balloon delivery device, and through improved physician training and experience with use of the drug-coated balloon and refinement of the treatment procedure. Further, it is to be expected that patient variability in anatomy and/or surgical history can lead to improved (or less beneficial) results.

Accordingly, in some embodiments of the present disclosure, treatment of polypoid edema with the drug-coated balloon can provide for a reduction of polyp size of at least 10%, and more specifically a reduction of polypoid edema burden from about 14% to about 35%. Similarly, in some embodiments of the of the present disclosure, treatment of polypoid edema with the drug-coated balloon can provide for a reduction of inflammation of the target tissue exhibiting polypoid edema of at least 10%, and more specifically a reduction of inflammation from about 16% to about 35%. Further, in some embodiments of the present disclosure, treatment of polypoid edema with the drug-coated balloon can provide for a reduced need for post-procedure oral steroid intervention by about 33% to about 50%.

Although the foregoing invention has, for the purposes of clarity and understanding been described in some detail by way of illustration and example, it will be apparent that certain changes and modifications can be practiced, and are intended to fall within the scope of the appended claims.

The invention claimed is:

1. A system for locally delivering a therapeutically effective amount of an active agent to a surface of a target tissue comprising:
   an expandable member sized and shaped for placement in an ear, nose, or throat of a patient, the expandable member comprising a drug layer at least partially covering an outer surface thereof, wherein:
   the drug layer comprises at least about 60% of mometasone furoate as drug crystals and the drug crystals have an average length greater than about 80 µm to maintain a therapeutically effective amount of at least 0.1 µg/gm of the mometasone furoate in the target tissue over a treatment period of at least 30 days; or
   the drug layer comprises less than about 60% of the mometasone furoate as drug crystals and the drug crystals have an average length less than about 80 µm to maintain the therapeutically effective amount of at least 0.1 µg/gm of the mometasone furoate in the target tissue over the treatment period of at least 30 days.

2. The system of claim 1, wherein a dose density of the mometasone furoate in the drug layer ranges from about 4 µg/mm$^2$ to about 8 µg/mm$^2$.

3. The system of claim 1, wherein the target tissue is a frontal sinus, a maxillary sinus, a sphenoid sinus, an ethmoid sinus, a sinus ostium, an inferior turbinate, a middle turbinate, a superior turbinate, a nasal cavity, the osteomeatal complex, the nasopharynx, adenoid tissue, ear tissue, or a combination thereof.

4. The system of claim 1, wherein the target tissue is the Eustachian tube, the external ear canal, or the middle ear.

5. The system of claim 1, wherein the target tissue is the tonsils, esophagus, trachea, larynx, or epiglottis.

6. The system of claim 1, wherein the expandable member is a balloon having an inflated configuration and a low-profile configuration.

7. The system of claim 6, wherein the balloon is configured to deliver the mometasone furoate over multiple transitions from the low-profile to the inflated configuration.

8. The system of claim 1, wherein the drug layer further comprises a poly(vinyl pyrrolidone), a polysorbate, a poly(ethylene glycol), propylene glycol, glycerol caproate, or combinations or mixtures thereof.

9. The system of claim 1, wherein the expandable member and the drug layer are configured to treat polypoid edema in a patient, mucosal inflammation in a patient, or a combination thereof.

10. The system of claim 1, wherein the mometasone furoate is therapeutically effective to treat polypoid edema at the target tissue site.

11. The system of claim 1, wherein the mometasone furoate is therapeutically effective to reduce the size of one or more nasal polyps at the target tissue site.

12. The system of claim 1, wherein the mometasone furoate is therapeutically effective to treat mucosal inflammation at the target tissue site.

* * * * *